(12) United States Patent
Timmers et al.

(10) Patent No.: US 7,674,909 B2
(45) Date of Patent: Mar. 9, 2010

(54) TETRAHYDROQUINOLINE DERIVATIVES AND THEIR USE AS FSH RECEPTOR MODULATORS

(75) Inventors: Cornelis Marius Timmers, Oss (NL); Willem Frederik Karstens, Oss (NL)

(73) Assignee: N.V. Organon, Oss (NL)

( * ) Notice: Subject to any disclaimer, the term of this patent is extended or adjusted under 35 U.S.C. 154(b) by 0 days.

(21) Appl. No.: 10/540,335

(22) PCT Filed: Dec. 16, 2003

(86) PCT No.: PCT/EP03/51024

§ 371 (c)(1),
(2), (4) Date: Jan. 10, 2006

(87) PCT Pub. No.: WO2004/056779

PCT Pub. Date: Jul. 8, 2004

(65) Prior Publication Data

US 2006/0167047 A1 Jul. 27, 2006

Related U.S. Application Data

(60) Provisional application No. 60/435,479, filed on Dec. 20, 2002.

(30) Foreign Application Priority Data

Dec. 20, 2002 (EP) .................................. 02102865

(51) Int. Cl.
*C07D 215/12* (2006.01)
*C07D 215/14* (2006.01)
*C07D 413/00* (2006.01)
*C07D 241/00* (2006.01)
*C07D 241/02* (2006.01)
*C07D 307/02* (2006.01)
*C07D 315/00* (2006.01)
*C07D 407/00* (2006.01)
*A01N 37/18* (2006.01)
*A61K 31/16* (2006.01)

(52) U.S. Cl. .................. 546/168; 544/128; 544/336; 549/473; 514/616

(58) Field of Classification Search .................. None
See application file for complete search history.

(56) References Cited

U.S. PATENT DOCUMENTS

| 2,686,182 A | 8/1954 | Hopff et al. .................. 260/287 |
| 6,200,963 B1 | 3/2001 | Wrobel et al. .............. 514/150 |
| 2006/0142334 A1 | 6/2006 | Timmers |

FOREIGN PATENT DOCUMENTS

| EP | 0303 306 B1 | 2/1989 |
| WO | WO 00/08015 | 2/2000 |

OTHER PUBLICATIONS

Rao. J. Biosci. vol. 26, No. 4, Nov. 2001, 425-427.*
Van Straten et al. J. Med. Chem. 2005, 48 (6), 1697-1700.*
Guo, Expert Opin. Ther. Patents (2005) 15(11).*
International Search Report, No. PCT/EP03/51024, Jun. 30, 2004.
Ronlad L. Atkins et al., "Substituted Coumarins and Azacoumarins. Synthesis and Fluorescent Properties," J. Org. Chem., vol. 43, No. 10, pp. 1975-1980 (1978).
Jay V. Johnson et al., "2,4-Diamino-5-benzylpyrimidines and Analogues as Antibacterial Agents. 12.1,2-Dihydroquinolymethyl Analogues with High Activity and Specificity for Bacterial Dihydrofolate Reductase," J. Med. Chem. vol. 32, pp. 1942-1949 (1989).
James P. Edwards et al., "5-Aryl-1,2-dihydro-5H-chromeno[3,4-f]quinolines as Potent, Orally Active, Nonsteroidal Progesterone Receptor Agonists: The Effect of D-Ring Substituents," J. Med. Chem. vol. 41, pp. 303-310 (1998).

(Continued)

Primary Examiner—Shaojia Anna Jiang
Assistant Examiner—Layla Bland
(74) Attorney, Agent, or Firm—Susan Hess

(57) ABSTRACT

The present invention relates to tetrahydroquinoline derivatives having general formula (I) or a pharmaceutically acceptable salt thereof, wherein $R^1$ and $R^2$ are H, Me; $R^3$ is (2-6C) heterocycloalkyl(1-4C)alkyl, (2-5C)heteroaryl(1-4C)alkyl, (6C)aryl (1-4C)alkyl, (1-4C)(di)alkylaminocarbonylamino (2-4C)alkyl, (2-6C) heterocycloalkylcarbonylamino(2-4C) alkyl, $R^5$-(2-4C)alkyl or $R^5$-carbonyl(1-4C)alkyl; $R^4$ is (2-5C)heteroaryl, (6C)aryl, (3-8C)cycloalkyl, (2-6C)heterocycloalkyl or (1-6C) alkyl and $R^5$ is (di)(1-4C)alkylamino, (1-4C)alkoxy, amino, hydroxy, (6C)arylamino, (di)(3-4C) alkenylamino, (2-5C)heteroaryl(1-4C)alkylamino, (6C)aryl (1-4C) alkylamino, (di)[(1-4C)alkoxy(2-4C)alkyl]amino, (di)[(1-4C)alkylamino(2-4C) alkyl]amino, (di)[amino(2-4C) alkyl]amino or (di)[hydroxy(2-4C)alkyl]amino. The present invention also relates to pharmaceutical compositions comprising said derivatives and the use of these derivatives to regulate fertility.

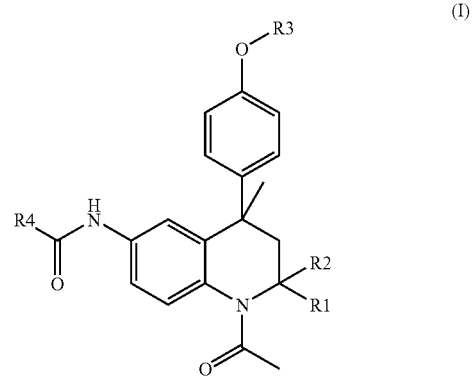

9 Claims, No Drawings

OTHER PUBLICATIONS

Lawrence G. Hamann et al., "Synthesis and Biological Activity of a Novel Series of Nonsteroidal, Peripherally Selective Androgen Receptor Antagonists Derived from 1,2-Dihydrophyridono[5,6-g]quinolines," J. Med. Chem, vol. 41, pp. 623-639 (1998).

Maria-Elena Theoclitou et al, "Novel facile synthesis of 2,2,4 substituted 1,2-dihydroquinolines via a modified Skraup reaction," Tetrahedron Letters 43, pp. 3907-3910 (2002).

Jennifer H. Dorrington et al., "Effects of FSH on Gonadal Functions," Recent Progress In Hormone Research, Vo. 35, pp. 301-342 (1979).

"Gonadotropin Therapy: New Trends and Insights," Int J. Fertil, vol. 33, pp. 85-97 (1988).

Richard M. Sharpe "Intratesticular Control of Steroidogenesis," Clinical Endocrinology, vol. 33, pp. 787-807 (1990).

Jane H. Morse et al., "Heterogeneity of Proteins in Commercial Preparations of Human Chorionic Gonadotropin (hCG) Demonstrated by Western Blotting," American Journal of Reproductive Immunology And Microbiology, vol. 17 pp. 134-140 (1988).

Wiebe Olijive et al., "Molecular biology and biochemistry of human recombinant follicle stimulating hormone (Puregon®)," Molecular Human Reproduction, vol. 2, No. 5, pp. 371-382 (1996).

Daniel Navot et al., "The Use of Follicle-Stimulating Hormone for Controlled Ovarian Hyperstimulation in in Vitro Fertilization," vol. 4, pp. 3-13 (1988).

"Successful in-vitro fertilisation and embryo transfer after treatment with recombinant human FSH," The Lancet, vol. 339, pp. 1170-1171 (1992).

U.S. Appl. No. 10/482,707, filed Jan. 2, 2004, Van Straten.

* cited by examiner

TETRAHYDROQUINOLINE DERIVATIVES AND THEIR USE AS FSH RECEPTOR MODULATORS

This application claims priority based on International Patent Application No. PCT/EP2003/051024, filed Dec. 16, 2003, European Patent Application No. 02102865.9, filed Dec. 20, 2002 and U.S. Provisional Patent Application No. 60/435,479, filed Dec. 20, 2002.

The invention relates to a compound having FSH receptor modulatory activity, in particular a tetrahydroquinoline derivative, to a pharmaceutical composition containing the same, as well as the use of said compound in medical therapy.

Gonadotropins serve important functions in a variety of bodily functions including metabolism, temperature regulation and the reproductive process. Gonadotropins act on specific gonadal cell types to initiate ovarian and testicular differentiation and steroidogenesis. The hypophyseal gonadotropin FSH (follicle stimulating hormone) for example plays a pivotal role in the stimulation of folicle development and maturation whereas LH (luteinizing hormone) induces ovulation (Sharp, R M. Clin Endocrinol. 33:787-807, 1990; Dorrington and Armstrong, Recent Prog. Horm. Res. 35:301-342, 1979). Currently, FSH is applied clinically, in combination with LH or hCG, for ovarian stimulation i.e. ovarian hyperstimulation for in vitro fertilization (IVF) and induction of ovulation in infertile anovulatory women (Insler, V., Int. J. Fertility 33:85-97, 1988, Navot and Rosenwaks, J. Vitro Fert. Embryo Transfer 5:3-13, 1988), as well as for male hypogonadism and male infertility.

The gonadotropin FSH is released from the anterior pituitary under the influence of gonadotropin-releasing hormone and oestrogens, and from the placenta during pregnancy. In the female, FSH acts on the ovaries promoting development of follicles and is the major hormone regulating secretion of oestrogens. In the male, FSH is responsible for the integrity of the seminiferous tubules and acts on Sertoli cells to support gametogenesis. Purified FSH is used clinically to treat infertility in females and for some types of failure of spermatogenesis in males. Gonadotropins destined for therapeutic purposes can be isolated from human urine sources and are of low purity (Morse et al, Amer. J. Reproduct. Immunol. and Microbiology 17:143, 1988). Alternatively, they can be prepared as recombinant gonadotropins. Recombinant human FSH is available commercially and is being used in assisted reproduction (Olijve et al. Mol. Hum. Reprod. 2:371, 1996; Devroey et al. Lancet 339:1170, 1992). The actions of the FSH hormone are mediated by a specific plasma membrane receptor that is a member of the large family of G-protein coupled receptors. These receptors consist of a single polypeptide with seven transmembrane domains and are able to interact with the Gs protein, leading e.g. to the activation of adenylate cyclase.

The FSH receptor is a highly specific target in the ovarian follicle growth process and is exclusively expressed in the ovary. Blocking this receptor or inhibiting the signaling which is normally induced after FSH-mediated receptor activation will disturb follicle development and thus ovulation and fertility. Low molecular weight FSH antagonists could therefore form the basis for new contraceptives. Such FSH antagonists could give rise to diminished follicle development (no ovulation) with still sufficient estrogen production left to avoid adverse effects on e.g. bone mass. On the other hand, compounds that stimulate FSH receptor activity may serve to mimic the gonadotropic effect of the natural ligand.

The present invention describes the preparation of low molecular weight hormone analogs that selectively have modulatory activity on the FSH receptor. The compounds of the invention can either be used as partial) agonists or (partial) antagonists of the FSH-receptor.

Thus, it has now been found, that the following class of tetrahydroquinoline compounds of formula I or pharmaceutically acceptable salts thereof have FSH-modulatory activity:

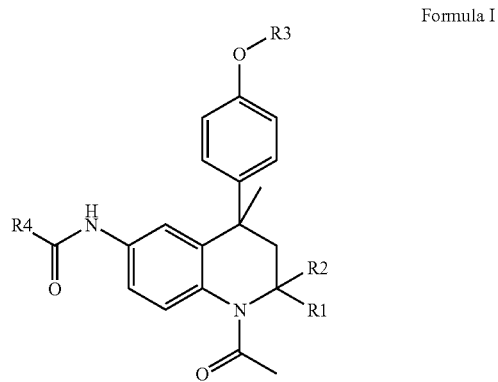

Formula I wherein
$R^1$ and $R^2$ are H, Me;
$R^3$ is (2-6C)heterocycloalkyl(1-4C)alkyl, (2-5C)heteroaryl (1-4C)alkyl, (6C)aryl(1-4C)alkyl, (1-4C)(di)alkylaminocarbonylamino(2-4C)alkyl, (2-6C)heterocycloalkylcarbonylamino(2-4C)alkyl, $R^5$-(2-4C)alkyl or $R^5$-carbonyl (1-4C)alkyl;
$R^4$ is (2-5C)heteroaryl, (6C)aryl, (3-8C)cycloalkyl, (2-6C)heterocycloalkyl or (1-6C)alkyl
$R^5$ is (di)(1-4C)alkylamino, (1-4C)alkoxy, amino, hydroxy, (6C)arylamino, (di)(3-4C)alkenylamino, (2-5C)heteroaryl (1-4C)alkylamino, (6C)aryl(1-4C)alkylamino, (di)[(1-4C) alkoxy(2-4C)alkyl]amino, (di)[(1-4C)alkylamino(2-4C) alkyl]amino, (di)[amino(2-4C)alkyl]amino or (di) [hydroxy(2-4C)alkyl]amino.

The compounds according to the present invention modulate the FSH receptor function and can be used for the same clinical purposes as native FSH if they behave like agonists, with the advantage that they display altered stability properties and may be administered differently. If they block the FSH receptor they can be used e.g. as a contraceptive agent.

Thus, the FSH-receptor modulators of the present invention may be used for treating infertility, for contraception and for treatment of hormone-dependent disorders such as breast cancer, prostate cancer, and endometriosis.

The following terms are intended to have the indicated meanings denoted below as used in the specification and claims.

The term (1-4C)alkyl as used herein means a branched or unbranched alkyl group having 1-4 carbon atoms, being methyl, ethyl propyl isopropyl, butyl sec-butyl and tert-butyl.

The term (2-4C)alkyl as used herein means a branched or unbranched alkyl group having 2-4 carbon atoms, being ethyl, propyl, isopropyl butyl, sec-butyl and tert-butyl.

The term (1-6C)alkyl as used herein means a branched or unbranched alkyl group having 1-6 carbon atoms, for example methyl, ethyl, propyl, isopropyl, butyl, sec-butyl tert-butyl and hexyl. (1-5C)Alkyl groups are preferred, (1-4C)alkyl being the most preferred.

The term (di)(1-4C)alkylamino as used herein means an amino group, monosubstituted or disubstituted with alkyl groups, each of which contains 1-4 carbon atoms and has the same meaning as previously defined.

The term (di)(1-4C)alkenylamino as used herein means an amino group, monosubstituted or disubstituted with alkenyl groups, each of which contains 2-4 carbon atoms such as allyl and 2-butenyl and has the same meaning as previously defined.

The term (3-8C)cycloalkyl as used herein means a cycloalkyl group having 3-8 carbon atoms, being cyclopropyl, cyclobutyl, cyclopentyl cyclohexyl, cycloheptyl and cyclooctyl. (3-6C)cycloalkyl groups are preferred.

The term (2-6C)heterocycloalkyl as used herein means a heterocycloalkyl group having 2-6 carbon atoms, preferably 3-5 carbon atoms, and at least including one heteroatom selected from N, O and/or S, which may be attached via a heteroatom if feasible, or a carbon atom. Preferred heteroatoms are N or O. The hetrocycloalkyl group may be substituted with a methyl or ethyl group at a carbon atom, or a heteroatom if feasible. Most preferred heterocycloalkyl groups are piperidinyl, piperazinyl, morpholinyl pyrrolidinyl and 1-methyl-2-piperidinyl.

The term (1-4C)alkoxy as used herein means an alkoxy group having 1-4 carbon atoms, the alkyl moiety having the same meaning as previously defined. (1-2C)Alkoxy groups are preferred.

The term (6C)aryl as used herein means a phenyl group, which may optionally be substituted with one or more substituents selected from hydroxy, amino, iodo, bromo, chloro, fluoro, nitro, trifluoromethyl cyano, phenyl, (1-4C)alkyl, (1-4C)alkoxy or (1-4C)(di)alkylamino, the alkyl, alkoxy and (di)alkylamino moieties having the same meaning as previously defined, for example phenyl 3,5-dibromophenyl, 4-biphenyl, 3,5-dichlorophenyl, 3-bromo-6-methylamino-phenyl, 3-chloro-2,6-dimethoxyphenyl and 3,5-dimethylphenyl.

The term (2-5C)heteroaryl as used herein means a substituted or unsubstituted aromatic group having 2-5 carbon atoms, at least including one heteroatom selected from N, O and/or S, like imidazolyl, pyridyl, pyrimidyl, thienyl or furyl. The substituents on the heteroaryl group may be selected from the group of substituents listed for the (6C)aryl group. The heteroaryl group may be attached via a carbon atom or a heteroatom, if feasible. Preferred heteroaryl groups are thienyl furyl and pyridyl.

The term (2-6C)heterocycloalkyl(1-4C)alkyl as used herein means a heterocycloalkyl group having 2-6 carbon atoms, connected to an alkyl group having 1-4 carbon atoms, the heterocycloalkyl group and the alkyl group having the same meaning as previously defined.

The term (2-6C)heterocycloalkylcarbonylamino as used herein means a heterocycloalkyl group having 2-6 carbon atoms, connected to the carbonyl moiety of a carbonylamino group, the heterocycloalkyl group having the same meaning as previously defined.

The term (2-6C)heterocycloalkylcarbonylamino(2-4C)alkyl as used herein means a heterocycloalkylcarbonylamino group of which the heterocycloalkyl moiety contains 2-6 carbon atoms, connected via the amino group to an alkyl group having 2-4 carbon atoms, the heterocycloalkylcarbonylamino group and the alkyl group having the same meaning as previously defined.

The term (di)(1-4C)alkylaminocarbonyl as used herein means a (di)alkylamino group, the alkyl group(s) of which having 14 carbon atoms, connected via the amino group to a carbonyl group, the (di)alkylamino group having the same meaning as previously defined.

The term (3-8C)cycloalkylaminocarbonyl as used herein means a cycloalkyl group having 3-8 carbon atoms, connected to the amino moiety of an aminocarbonyl group, the cycloalkyl group having the same meaning as previously defined.

The term (di)(1-4C)alkaminocarbonylamino as used herein means a (di)alkylamino group, the alkyl group(s) of which having 1-4 carbon atoms, connected via the amino group to the carbonyl moiety of a carbonylamino group, thus providing a urea functionality, the (di)alkylamino group having the same meaning as previously defined.

The term (di)(1-4C)alkylaminocarbonylamino(2-4C)alkyl as used herein means a (di)alkylaminocarbonylamino group, the alkyl group(s) of which having 14 carbon atoms, connected via the amino group to an alkyl group having 2-4 carbon atoms, the (di)alkylaminocarbonylamino group and the alkyl group having the same meaning as previously defined.

The term (2-5C)heteroaryl(1-4C)alkyl as used herein means a heteroaryl group having 2-5 carbon atoms connected to an alkyl group having 1-4 carbon atoms, the heteroaryl group and the alkyl group having the same meaning as previously defined.

The term (6C)aryl(1-4C)alkyl as used herein means phenyl group, optionally substituted with one or more substituents selected from the group of substituents listed for the (6C)aryl group, connected to an alkyl group having 14 carbon atoms, the aryl group and the alkyl group having the same meaning as previously defined.

The term (6C)arylamino as used herein means phenyl group, optionally substituted with one or more substituents selected from the group of substituents listed for the (6C)aryl group, connected to an amino group, the aryl group having the same meaning as previously defined.

The term (6C)aryl(1-4C)alkylamino as used herein means phenyl group, optionally substituted with one or more substituents selected from the group of substituents listed for the (6C)aryl group, connected to the allyl moiety of an alkylamino group having 1-4 carbon atoms, the aryl group and the alkylamino group having the same meaning as previously defined.

The term (2-5C)heteroaryl(1-4C)alkylamino as used herein means a heteroaryl group having 2-5 carbon atoms, optionally substituted with one or more substituents selected from the group of substituents listed for the (6C)aryl group, connected to the alkyl moiety of an alkylamino group having 14 carbon atoms, the heteroaryl group and the alkylamino group having the same meaning as previously defined.

The term (1-4C)alkoxy(2-4C)alkyl as used herein means an alkoxy group having 1-4 carbon atoms, connected to an alkyl group having 2-4 carbon atoms, the alkoxy group and alkyl group having the same meaning as previously defined The term (di)[(1-4C)alkoxy(2-4C)alkyl]amino as used herein means an amino group, monosubstituted or disubstituted with (1-4C)alkoxy(2-4C)alkyl groups. The (1-4C)alkoxy(2-4C)alkyl group is an alkoxy group having 1-4 carbon atoms, connected to an alkyl group having 2-4 carbon atoms and has the same meaning as previously defined.

The term (1-4C)alkylamino(2-4C)alkyl as used herein means an alkylamino group is having 1-4 carbon atoms, connected via the amino group to an allyl group having 2-4 carbon atoms, the alkyl moieties having the same meaning as previously defined.

The term (di)[(1-4C)alkylamino(2-4C)alkyl]amino as used herein means an amino group, monosubstituted or disubstituted with (1-4C)alkylamino(2-4C)alkyl groups. The (1-4C)alkylamino(2-4C)alkyl group is an alkylamino group having 1-4 carbon atoms, connected via the amino group to an alkyl group having 2-4 carbon atoms and has the same meaning as previously defined.

The term amino(2-4C)alkyl as used herein means an aminoalkyl group having 2-4 carbon atoms, the alkyl moiety having the same meaning as previously defined.

The term (di)[amino(2-4C)alkyl]amino as used herein means an amino group, monosubstituted or disubstituted with aminoalkyl groups having 24 carbon atoms and having the same meaning as previously defined.

The term hydroxy(2-4C)alkyl as used herein means an hydroxyalkyl group having 2-4 carbon atoms, the alkyl moiety having the same meaning as previously defined.

The term (di)[hydroxy(2-4)alkyl]amino as used herein means an amino group, monosubstituted or disubstituted with hydroxyalkyl groups, having 2-4 carbon atoms and having the same meaning as previously defined.

The term $R^5$-(2-4C)alkyl as used herein means a $R^5$ group attached to an alkyl moiety having 2-4 carbon atoms which has the same meaning as previously defined.

The tem $R^5$-carbonyl-(1-4C)alkyl as used herein means a $R^5$ group attached to the carbonyl moiety of a carbonylalkyl group, the alkyl moiety having 1-4 carbon atoms and having the same meaning as previously defined.

The term pharmaceutically acceptable salt represents those salts which are, within the scope of medical judgement, suitable for use in contact for the tissues of humans and lower animals without undue toxicity, irritation, allergic response and the like, and are commensurate with a reasonable benefit/risk ratio. Pharmaceutically acceptable salts are well known in the art. They may be obtained during the final isolation and purification of the compounds of the invention, or separately by reacting a flee base function, if present, with a suitable mineral acid such as hydrochloric acid, phosphoric acid, or sulfuric acid, or with an organic acid such as for example ascorbic acid, citric acid, tartric acid, lactic acid, maleic acid, malonic acid, fumaric acid, glycolic acid, succinic acid, propionic acid, acetic acid, methanesulfonic acid, and the like. If present, an acid function can be reacted with an organic or a mineral base, like sodium hydroxide, potassium hydroxide or lithium hydroxide.

The invention thus relates to the compounds of Formula I as defined here above.

In another embodiment the invention provides compounds according to Formula I wherein $R^1$ and $R^2$ are Me.

The invention also relates to compounds of formula I, wherein $R^3$ is (2-6C)heterocycloalkyl(1-4C)alkyl, (2-5C)heteroaryl(1-4C)alkyl, (2-6C)heterocycloalkylcarbonylamino(2-4C)alkyl, $R^5$-(2-4C)alkyl, $R^5$-carbonyl(1-4C)alkyl.

In another aspect the invention concerns compounds according to Formula I wherein $R^3$ is (2-6C)heterocycloalkyl(1-4C)alkyl, (2-5C)heteroaryl(1-4C)alkyl, $R^5$-(2-4C)alkyl, $R^5$-carbonyl(1-4C)alkyl.

In yet another aspect the invention relates to compounds according to Formula I wherein $R^3$ is (2-6C)heterocycloalkyl(1-4C)alkyl, (2-5C)heteroaryl(1-4C)alkyl or $R^5$-(2-4C)alkyl.

In another aspect the invention relates to compounds according to Formula I wherein $R^3$ is (2-6C)heterocycloalkyl(1-4C)alkyl.

According to yet another embodiment of the invention the heterocycloalkyl group in heterocycloalkyl(1-4C)alkyl in $R^3$ according to Formula I consists of 4, 5 or 6 C atoms and the heteroaryl group in heteroaryl(1-4C)alkyl in $R^3$ consists of 3, 4 or 5 C atoms.

In another embodiment the invention relates to compounds according to Formula I, wherein $R^4$ is (6C)aryl.

In yet another embodiment the invention provides compounds of Formula I wherein $R^5$ is (di)(1-4C)alkylamino, amino, (di)(3-4C)alkenylamino, (2-5C)heteroaryl(1-4C)alkylamino, (6C)aryl(1-4C)alkylamino, (di)[(1-4C)alkoxy(2-4C)alkyl]amino, (di)[(1-4C)alkylamino(2-4C)alkyl]amino, (di)[amino(2-4C)alkyl]amino, (di)[hydroxy(2-4C)alkyl]amino.

In another aspect the invention relates to compounds according to Formula I wherein $R^5$ is (di)(1-4C)alkylamino, (2-5C)heteroaryl(1-4C)alkylamino, (di)[(1-4C)alkoxy(2-4C)alkyl]amino, (di)[(1-4C)alkylamino(2-4C)alkyl]amino, (di)[amino(2-4C)alkyl]amino or (di)[hydroxy(2-4C)alkyl]amino.

In another aspect the invention relates to compounds according to Formula I wherein $R^5$ is (di)(1-4C)alkylamino, amino, (di)(3-alkenylamino, (2-5C)heteroaryl(1-4C)alkylamino, (6C)aryl(1-4C)alkylamino.

Another aspect of the invention are compounds according to Formula I wherein $R^5$ is (di)(1-4C)alkylamino or amino.

In yet another aspect of the invention, there are provided compounds according to Formula I wherein $R^5$ is (di)(1-4C)alkylamino.

Yet another aspect of the invention concerns compounds wherein all specific definitions of the groups $R^1$ through $R^5$ as defined here above are combined in the compound of Formula I.

Suitable methods for the preparation of the compounds of the invention are outlined below.

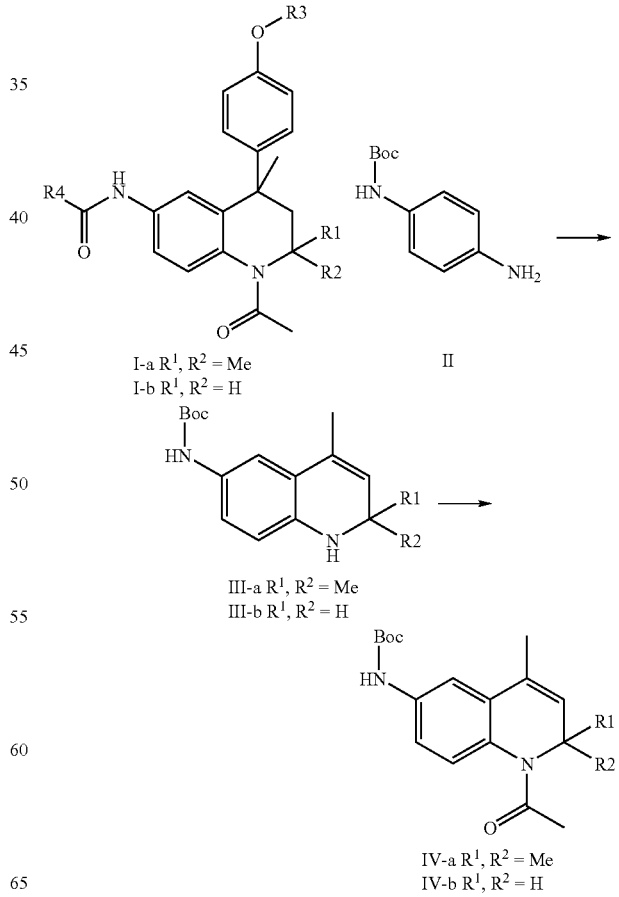

The compounds of the present invention with formula I-a can be prepared starting with the well-documented Skraup reaction. Performing this reaction on N-tert-butoxycarbonyl (N-Boc) protected 1,4-phenylenediamine (II) gives 1,2-dihydroquinoline derivative III-a.

Related Skraup cyclocondensation reactions are found in literature: A. Knoevenagel, Chem. Ber. 54:1726, 1921; R. L. Atkins and D. E. Bliss, J. Org. Chem. 43:1975, 1978; J. V. Johnson, B. S. Rauckman, D. P. Baccanari and B. Roth, J. Med. Chem. 32:1942, is 1989; W. C. Lin, S.-T. Huang and S.-T. Lin, J. Chin. Chem. Soc. 43:497, 1996; J. P. Edwards, S. J. West K. B. Marschke, D. E. Mais, M. M. Gottardis and T. K Jones, J. Med. Chem. 41:303, 1998.

The abovementioned reaction is typically conducted at elevated temperature in acetone or mesityl oxide in the presence of iodine or protic acid such as hydrochloric acid, p-toluenesulfonic acid or aqueous hydrogen iodide. Alternatively, the compound of formula III-a can be prepared by reacting compound II with acetone in the presence of $MgSO_4$, 4-tert-butylcatechol and iodine (L. G. Hamann, R. I. Higuchi, L. Zhi, J. P. Edwards and X.-N. Wang, J. Med. Chem, 41:623, 1998). In yet another procedure, the reaction can be performed in acetone using lanthanide triflates (e.g. scandium triflate) as catalysts. In this case, the reaction can be run at room temperature or at elevated temperatures using conventional heating or microwave irradiation (M. E. Theoclitou and L. A. Robinson, Tetrahedron Lett. 43:3907, 2002).

The compound of formula III-b can be prepared from N-Boc-1,4-phenylenediamine II by reaction with methyl vinyl ketone. Related cyclizations are described in U.S. Pat. No. 2,686,182 (Badische Anilin- & Soda-Fabrik Aktiengesellschaft).

Subsequent 1-N-acetylation of the compounds of formula III-a-b can be carried out using standard conditions. In a typical experiment, compounds of formula III-a-b are heated under reflux in acetic anhydride or reacted in a solvent such as dichloromethane, tetrahydrofuran, toluene or pyridine with acetyl chloride in the presence of a base such as N,N-diisopropylethylamine, triethylamine or sodium hydride to give the 1-N-acetyl-4-methyl-1,2-dihydroquinoline derivatives of formula IV-a-b.

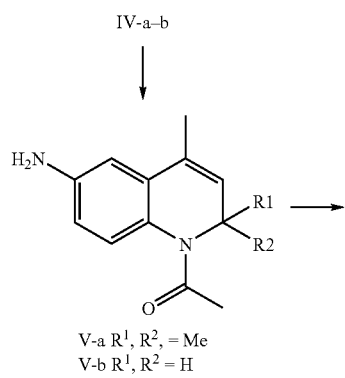

V-a $R^1, R^2$, = Me
V-b $R^1, R^2$ = H

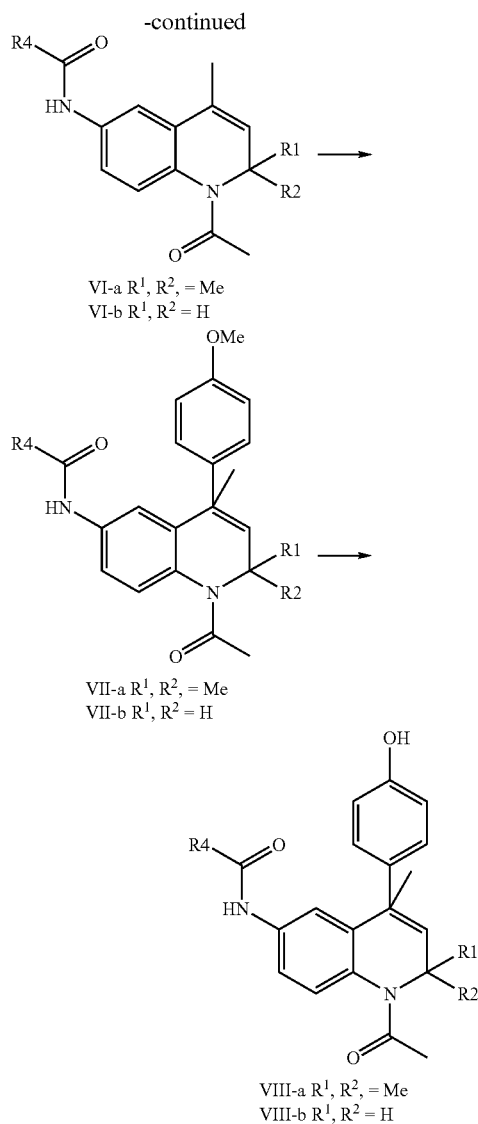

VI-a $R^1, R^2$, = Me
VI-b $R^1, R^2$ = H

VII-a $R^1, R^2$, = Me
VII-b $R^1, R^2$ = H

VIII-a $R^1, R^2$, = Me
VIII-b $R^1, R^2$ = H

Standard cleavage of the Boc protective group under conditions well known to those skilled in the art affords the 6-amino-1,2-dihydroquinoline derivatives of formula V-a-b. This reaction is typically conducted in dichloromethane in the presence of trifluoroacetic acid.

Subsequent 6-N-acylation of the compounds of formula V-a-b can be carried out using standard conditions to give compounds of general formula VI-a-b, wherein $R^4$ is as previously defined. For example, compounds of formula V-a-b are reacted in a solvent such as dichloromethane, tetrahydrofuran or toluene with an acyl halide ($R^4$—C(O)—Cl) or acid anhydride ($R^4$—C(O)—O—C(O)—$R^4$) in the presence of a base such as N,N-diisopropylethylamine, triethylamine, pyridine or sodium hydride to give 6-N-acylated 4-methyl-1,2-dihydroquinoline derivatives of formula VI-a-b. Alternatively, acylation of compounds of general formula V-a-b to give compounds of general formula VI-a-b can also be accomplished by reaction with an appropriate carboxylic acid ($R^4$—$CO_2H$) in the presence of a coupling reagent such as O-(benzotriazol-1-yl)-N,N,N',N'-tetramethyluronium tetrafluoroborate (TBTU), O-(7-azabenzotriazol-1-yl)-N,N,N,', N'-tetramethyluronium hexafluorophosphate (HATU) or bromotripyrrolidinophosphonium hexafluorophosphate (PyBrOP) and a tertiary base, e.g. N,N-diisopropylethylamine, in a solvent such as N,N-dimethylformamide or dichloromethane at ambient or elevated temperature.

Introduction of the requisite substituted phenyl group at position 4 of the dihydroquinoline scaffold can be accomplished via Friedel-Crafts alkylation of anisole with the compounds of general structure VI-a-b to yield compounds of general formula VII-a-b. This reaction is typically conducted at elevated temperatures either in anisole or in an appropriate inert solvent such as heptane or hexane with anisole as reagent, under catalysis of a Lewis acid (e.g. $AlCl_3$, AlBr3, $FeCl_3$ or $SnCl_4$). Friedel-Crafts alkylations with 2,2,4-trimethyl-1,2-dihydroquinolines are described in literature by B. A. Lugovik, L. G. Yudin and A. N. Kost, Dokl. Akad. Nauk SSSR, 170:340, 1966; B. A. Lugovik, L. G. Yudin, S. M. Vinogradova and A. N. Kost, Khim. Geterosikl. Soedin, 7:795, 1971.

Alternatively, N-Boc-1,4-phenylenediamine II can be reacted with 2-(4-methoxyphenyl)-propene and formaldehyde in acetonitrile at ambient or elevated temperature, followed by 1-N-acetylation as described previously, to give the compound VII-b in which $R^4$=O-tert-Bu. Related cyclizations are described in literature: J. M. Mellor and G. D. Merriman, Tetrahedron, 51:6115, 1995. Cleavage of the Boc protective group and subsequent acylation of the 6-amino function with an acyl halide ($R^4$—C(O)—Cl) as described before gives access to compounds of general structure VII-b in which $R^4$ is as described previously.

Cleavage of the aromatic methyl ether in compounds of general formula VII-a-b affords 4-(4-hydroxyphenyl) substituted tetrahydroquinoline derivatives of general formula VIII-a-b, setting the stage for functionalization of the free OH group.

R3—X +
IX-a: X = Cl, Br, I
IX-b: X = OH

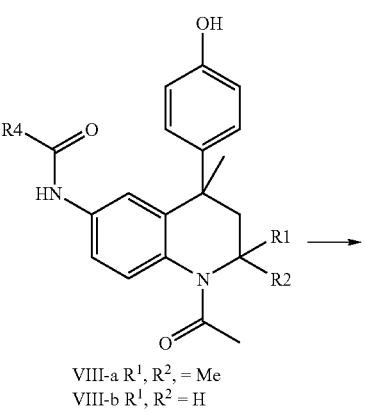

VIII-a $R^1, R^2, =$ Me
VIII-b $R^1, R^2 =$ H

-continued

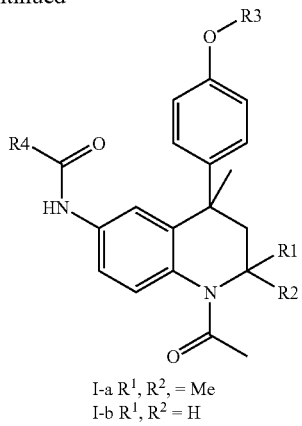

I-a $R^1, R^2, =$ Me
I-b $R^1, R^2 =$ H

Demethylation reactions of aromatic methyl ethers are well known to those skilled in the art. In a typical experiment, demethylation is achieved upon reaction of a compound of formula VII-a-b with $BBr_3$ in an inert solvent such as dichloromethane at low to ambient temperature to give demethylated compounds of general formula VIII-a-b. Alternatively, demethylation can be accomplished upon reaction of compounds of formula VII-a-b with $BF_3.Me_2S$ complex at ambient temperature.

Selective O-alkylation of compounds of general formula VIII-a-b with functionalized alkyl halides of general formula IX-a, leads to the formation of compounds with general formula I-a-b. Alkylation reactions of aromatic hydroxyl groups are well is known in the art. Typically, a solution of a compound of general formula VIII-a-b in a suitable solvent such as 1,4-dioxane, tetrahydrofuran, dichloromethane, acetonitrile, acetone or N,N-dimethylformamide is treated with a base (e.g. N,N-diisopropylamine, triethylamine, $K_2CO_3$, $Cs_2CO_3$ or NaOH) and the appropriate alkylation reagent of general formula IX-a, for example benzyl bromide, 3-(dimethylamino)-propyl chloride, 4-(2-chloroethyl)-morpholine, 2-picolylchloride or 2-chloroacetamide. Alternatively, alkylation can be accomplished by the known Mitsunobu-type alkylation. In that case a solution of a compound of general formula VIII-a-b in a suitable solvent such as 1,4-dioxane, tetrahydrofuran, or dichloromethane is treated with (resin bound) triphenyl phosphine, diethyl- or di-tert-butyl azodicarboxylate and a functionalized alcohol of general formula IX-b. In principle, both allylation methods can be used for au $R^3$ groups, but a suitable protective group strategy may be required if $R^3$ contains a nucleophilic group such as a secondary amine or a hydroxyl group. Selection of a protective group and deprotection conditions are trivial to those skilled in the art.

Another procedure to obtain compounds of the current invention starts with the allylation of compounds of general formula VIII-a-b with esters of general formula X.

The alkylation reaction is typically conducted in the presence of a base such as N,N-diisopropylethylamine or sodium hydride in a suitable solvent such as N,N-dimethylformamide or tetrahydrofuran at ambient or elevated temperature. The ester function in the resulting compounds of general formula XIII-a-b in which A=Me or Et can then selectively be reduced under controlled conditions to afford compounds of general formula XIII-a-b using an appropriate reducing agent such as lithium aluminum hydride at low temperature or sodium borohydride in an inert solvent such as tetrahydrofuran. The free hydroxyl group in compounds of general formula XIII-a-b may subsequently be reacted with 4-toluenesulfonyl chloride (Ts-Cl) or methanesulfonyl choride (Ms-Cl) in an inert solvent such as 1,4-dioxane, N,N-dimethylformamide or TBF in the presence of a suitable base such as triethylamine or pyridine to generate an appropriate leaving group (compounds of general formula XIV-a-b; LG=Ts or Ms, respectively). Nucleophilic substitution with an appropriate nucleophile (amine or alkoxide) under conditions known to those skilled in the art then gives access to compounds of general formula I-a-b in which $R^3=R^5$-(2-4C)alkyl and $R^5$ is as defined previously.

Conversion of compounds of general formula XI-a-b in which A=tert-Bu to carboxylic acids of general formula XII-a-b may be effected by deprotection of the tert-butyl ester function. In a typical experiment, the tert-butyl ester of general formula XI-a-b (A=tert-Bu) is dissolved in dichloromethane and treated with a strong acid such as trifluoroacetic acid. The resulting carboxylic acids of general formula XII-a-b may then be condensed with an appropriate alcohol or amine in the presence of a coupling agent such as O-(benzotriazol-1-yl)-N,N,N',N'-tetramethyluronium tetrafluoroborate (IBTU), O-(7-azabenzotriazol-1-yl)-N,N,N',N'-tetramethyluronium hexafluorophosphate (HATU) or bromotripyrrolidinophosphonium hexafluorophosphate (Py-BrOP) and a tertiary base, e.g. N,N-diisopropylethylamine, in a solvent such as N,N-dimethylformamide or dichloromethane at ambient or elevated temperature to give compounds of general formula I-a-b in which $R^3=R^5$-carbonyl (1-4C)alkyl and $R^5$ is as defined previously.

X

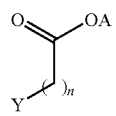

A = Me, Et, t-Bu
n = 1, 2, 3, 4
Y = I, Br, Cl

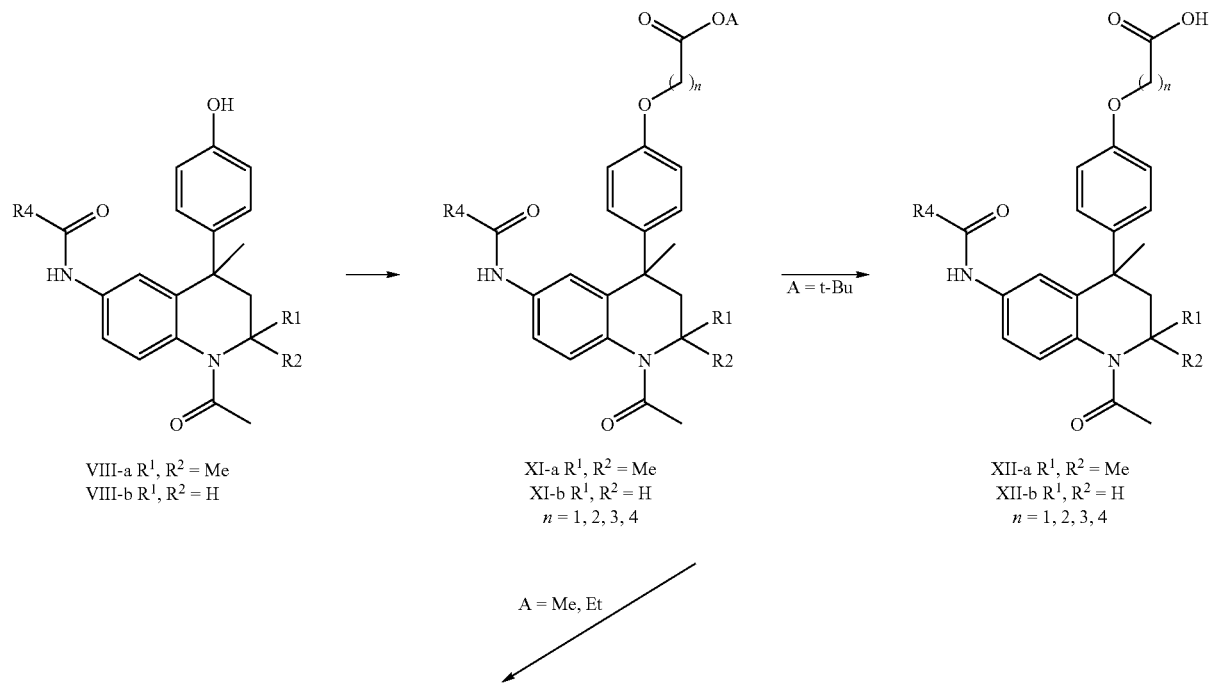

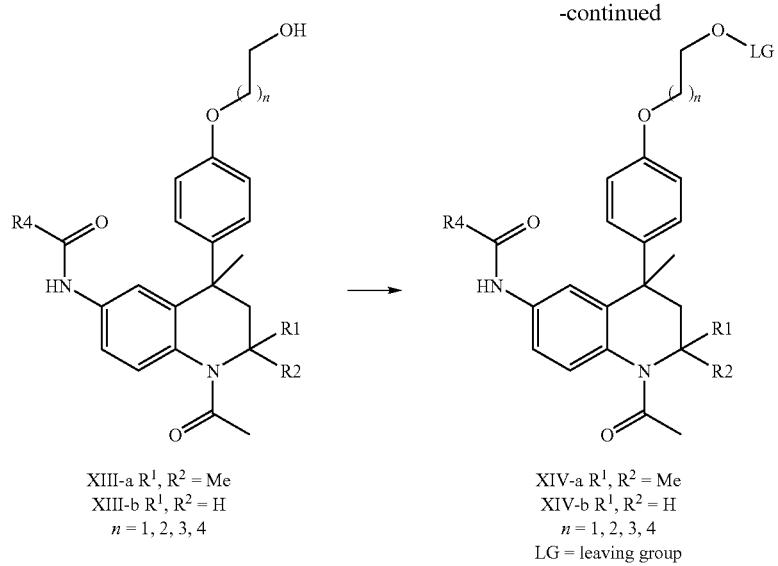

XIII-a R$^1$, R$^2$ = Me  
XIII-b R$^1$, R$^2$ = H  
n = 1, 2, 3, 4

XIV-a R$^1$, R$^2$ = Me  
XIV-b R$^1$, R$^2$ = H  
n = 1, 2, 3, 4  
LG = leaving group I-a R$^1$, R$^2$ = Me  
I-b R$^1$, R$^2$ = H Some of the compounds of the invention, which can be in the form of a free base, may be isolated from the reaction mixture in the form of a pharmaceutically acceptable salt. The pharmaceutically acceptable salts may also be obtained by treating the free base of formula I with an organic or inorganic acid such as hydrogen chloride, hydrogen bromide, hydrogen iodide, sulfuric acid, phosphoric acid, acetic acid, propionic acid, glycolic acid, maleic acid, malonic acid, methanesulphonic acid, fumaric acid, succinic acid, tartaric acid, citric acid, benzoic acid, and ascorbic acid.

The compounds of the present invention possess at least one chiral carbon atom and may therefore be obtained as pure enantiomers, or as a mixture of enantiomers, or as a mixture of diastereomers. Methods for obtaining the pure enantiomers are well known in the art, e.g crystallization of salts which are obtained from optically active acids and the racemic mixture, or chromatography using chiral columns. For diastereomers, straight phase or reversed phase columns may be used.

The compounds of the invention may form hydrates or solvates. It is known to those of skill in the art that charged compounds form hydrated species when lyophilized with water, or form solvated species when concentrated in a solution with an appropriate organic solvent. The compounds of this invention include the hydrates or solvates of the compounds listed.

For selecting active compounds testing at $10^{-5}$ M must result in an activity of more than 20% of the maximal activity when FSH is used as a reference. Another criterion might be the EC$_{50}$ value which must be $<10^{-5}$ M, preferably $<10^{-7}$ M.

The skilled artisan will recognize that desirable EC$_{50}$ values are dependent on the compound tested. For example, a compound with an EC$_{50}$ which is less than $10^{-5}$ M is generally considered a candidate for drug selection. Preferably this value is lower than $10^{-7}$ M. However, a compound which has a higher EC$_{50}$, but is selective for the particular receptor, may be even a better candidate.

Methods to determine receptor binding, as well as in vitro and in vivo assays to determine biological activity, of gonadotropins are well known. In general, the expressed receptor is contacted with the compound to be tested and binding or stimulation or inhibition of a functional response is measured.

To measure a functional response, isolated DNA encoding the FSH receptor gene, preferably the human receptor, is expressed in suitable host cells. Such a cell might be the Chinese Hamster Ovary cell, but other cells are also suitable. Preferably the cells are of mammalian origin (Jia et al, Mol. Endocrin., 5:759-776, 1991).

Methods to construct recombinant FSH expressing cell lines are well known in the art (Sambrook et al., Molecular Cloning: a Laboratory Manual, Cold Spring Harbor Laboratory Press, Cold Spring Harbor, latest edition). Expression of receptor is attained by expression of the DNA encoding the desired protein. Techniques for site directed mutagenesis, ligation of additional sequences, PCR, and construction of suitable expression systems are all, by now, well known in the art. Portions, or all, of the DNA encoding the desired protein can be constructed synthetically using standard solid phase techniques, preferably to include restriction sites for ease of ligation. Suitable control elements for transcription and translation of the included coding sequence can be provided to the DNA coding sequences. As is well known, expression systems are now available which are compatible with a wide variety of hosts, including prokaryotic hosts such as bacteria and eukaryotic hosts such as yeast, plant cells, insect cells, mammalian cells, avian cells and the like.

Cells expressing the receptor are then contacted with the test compound to observe binding, or stimulation or inhibition of a functional response.

Alternatively, isolated cell membranes containing the expressed receptor may be used to measure binding of compound.

For measurement of binding, radioactively labeled or fluorescently labeled compounds may be used. Also competition binding assays can be performed.

Another assay involves screening for FSH receptor agonist compounds by determining stimulation of receptor mediated cAMP accumulation. Thus, such a method involves expression of the receptor on the cell surface of a host cell and exposing the cell to the test compound. The amount of cAMP is then measured. The level of cAMP can be reduced or increased, depending on the inhibitory or stimulating effect of the test compound upon binding to the receptor.

Screening for FSH receptor antagonists involves incubation of FSH receptor-expressing cells with a concentration range of the test compound in the presence of a fixed, submaximally effective, FSH concentration (i.e., a FSH concentration that induces approximately 80% of the maximal stimulation of cAMP accumulation in the absence of test compound). From the concentration-effect curves, the $IC_{50}$ value and the percentage of inhibition of FSH-induced cAMP accumulation can be determined for each of the test compounds. As reference compound human recombinant FSH can be used. In the alternative also competition assays can be performed.

In addition to direct measurement of e.g. cAMP levels in the exposed cell, cells lines can be used which in addition to transfection with receptor encoding DNA are also transfected with a second DNA encoding a reporter gene the expression of which responds to the level of cAMP. Such reporter genes might be cAMP inducible or might be constructed in such a way that they are connected to novel cAMP responsive elements. In general, reporter gene expression might be controlled by any response element reacting to changing levels of cAMP. Suitable reporter genes are e.g. the genes encoding β-galactosidase, alkaline phosphatase, firefly luciferase and green fluorescence protein. The principles of such transactivation assays are well known in the art and are described e.g. in Stratowa, Ch., Himmler, A. and Czernilofsky, A. P., (1995) Curr. Opin. Biotechnol. 6:574.

The present invention also relates to a pharmaceutical composition comprising a tertrahydroquinoline derivative or pharmaceutically acceptable salts thereof having the general formula I in admixture with pharmaceutically acceptable auxiliaries and optionally other therapeutic agents. The auxiliaries must be "acceptable" in the sense of being compatible with the other ingredients of the composition and not deleterious to the recipients thereof.

Compositions include e.g. those suitable for oral, sublingual, subcutaneous, intravenous, intramuscular, local, or rectal administration, and the like, all in unit dosage forms for administration.

For oral administration, the active ingredient may be presented as discrete units, such as tablets, capsules, powders, granulates, solutions, suspensions, and the like.

For parenteral administration, the pharmaceutical composition of the invention may be presented in unit-dose or multi-dose containers, e.g. injection liquids in predetermined amounts, for example in sealed vials and ampoules, and may also be stored in a freeze dried (lyophilized) condition requiring only the addition of sterile liquid carrier, e.g. water, prior to use.

Mixed with such pharmaceutically acceptable auxiliaries, e.g. as described in the standard reference, Gennaro, A. R et al., Remington: *The Science and Practice of Pharmacy* (20th Edition., Lippincott Williams & Wilkins, 2000, see especially Part 5: Pharmaceutical Manufacturing), the active agent may be compressed into solid dosage units, such as pills, tablets, or be processed into capsules or suppositories. By means of pharmaceutically acceptable liquids the active agent can be applied as a fluid composition, e.g. as an injection preparation, in the form of a solution, suspension, emulsion, or as a spray, e.g. a nasal spray.

For making solid dosage units, the use of conventional additives such as fillers, colorants, polymeric binders and the like is contemplated. In general any pharmaceutically acceptable additive which does not interfere with the function of the active compounds can be used. Suitable carriers with which the active agent of the invention can be administered as solid compositions include lactose, starch, cellulose derivatives and the like, or mixtures thereof, used in suitable amounts. For parenteral administration, aqueous suspensions, isotonic saline solutions and sterile injectable solutions may be used, containing pharmaceutically acceptable dispersing agents and/or wetting agents, such as propylene glycol or butylene glycol.

The invention further includes a pharmaceutical composition, as hereinbefore described, in combination with packaging material suitable for said composition, said packaging material including instructions for the use of the composition for the use as hereinbefore described.

The tetrahydroquinoline derivatives of the invention can also be administered in the form of implantable pharmaceutical devices, consisting of a core of active material, encased by a release rate-regulating membrane. Such implants are to be applied subcutaneously or locally, and will release the active ingredient at an approximately constant rate over relatively large periods of time, for instance from weeks to years. Methods for the preparation of implantable pharmaceutical devices as such are known in the art, for example as described in European Patent 0,303,306 (AKZO Nobel N.V.).

The exact dose and regimen of administration of the active ingredient, or a pharmaceutical composition thereof, will necessarily be dependent upon the therapeutic effect to be achieved (treatment of infertility; contraception), and may vary with the particular compound, the route of administration, and the age and condition of the individual subject to whom the medicament is to be administered.

In general parenteral administration requires lower dosages than other methods of administration which are more dependent upon absorption. However, a dosage for humans preferably contains 0.0001-25 mg per kg body weight. The desired dose may be presented as one dose or as multiple subdoses administered at appropriate intervals throughout the day, or, in case of female recipients, as doses to be administered at appropriate daily intervals throughout the menstrual cycle. The dosage as well as the regimen of administration may differ between a female and a male recipient.

Thus, the compounds according to the invention can be used in therapy.

A further aspect of the invention resides in the use of a tetrahydroquinoline derivative compound having the general formula I for the manufacture of a medicament to be used for the treatment of disorders responsive to FSH receptor mediated pathways. Thus, patients in need thereof can be administered with suitable amounts of the compounds according to the invention.

In another aspect the invention resides in the use of a tetrahydroquinoline derivative compound having the general formula I for the manufacture of a medicament to be used for the control of fertility.

In yet another aspect the invention resides in the use of a tetrahydroquinoline derivative compound having the general formula I for the manufacture of a medicament to be used for the treatment of infertility.

In still another aspect the invention resides in the use of a tetrahydroquinoline derivative compound having the general formula I for the manufacture of a medicament to be used to prevent fertility.

The compounds according to the invention can also be used for the treatment of hormone-dependent disorders such as breast cancer, prostate cancer and endometriosis. The invention is illustrated by the following examples.

EXAMPLES

General Comments

The following abbreviations are used in the examples: DMA=N,N-dimethylaniline, DIPEA=N,N-diisopropylethylamine; TFA=trifluoroacetic acid, DtBAD=di-tert-butyl azodicarboxylate; TBTU=O-Benzotrazole-1-yl-N,N,N',N'-tetramethyluronium tetrafluoroborate; HATU=O-(7-azabenzotriazole-1-yl)-N,N,N',N'-tetramethyluronium hexafluorophosphate; Fmoc=9-fluorenylmethoxycarbonyl; Fmoc-Cl=9-fluorenylmethoxycarbonylchloride; DMF=N,N-dimethylformamide; Boc=tert-butoxycarbonyl; TBF=tetrahydrofuran.

The names of the final products described in the examples are generated using the Beilstein Autonom program (version: 2.02.119).

Unless stated otherwise, all final products of the examples below are lyophilized from water/1,4-dioxane mixtures or water/acetonitrile mixtures. If the compound was prepared as a HCl- or TFA salt, the respective acids were added in appropriate amounts to the solvent mixture before lyophilization.

The following analytical HPLC methods are used for determination of retention times:

Method 1: Column: 5 µm Luna C-18(2) 150×4.6 mm; flow: 1 ml/min; detection: 210 nm: column temperature: 40° C.; solvent A: $CH_3CN/H_2O=1/9$ (v/v); solvent B: $CH_3CN$; solvent C, 0.1 M aqueous trifluoroacetic acid; gradient: solvent A/B/C=65/30/5 to 10/85/5 (v/v/v) in 30.00 min, then constant for an additional 10.00 min at A/B/C=10/85/5 (v/v/v).

Method 2: Identical to method 1, except for the gradient used: Gradient: solvent A/B/C=75/20/5 to 15/80/5 (v/v/v) in 30.00 min, then constant for an additional 10.00 min at A/B/C=15/80/5 (v/v/v).

Method 3: Column: 3 µm Luna C-18(2) 100×2 mm; flow: 0.25 ml/min; detection: 210 nm; column temperature: 40° C.; solvent A: $H_2O$; solvent B: $CH_3CN$; solvent C: 50 mM phosphate buffer, pH 2.1; gradient: solvent A/B/C=70/20/10 to 10/80/10 (v/v/v) in 20.00 min, then constant for an additional 10.00 min at A/B/C=10/80/10 (v/v/v).

Method 4: Identical to method 3, except for the gradient used: Gradient: solvent A/B/C=65/30/5 to 10/85/5 (v/v/v) in 20.00 min, then constant for an additional 10.00 min at A/B/C=10/85/5 (v/v/v).

Method 5: Identical to method 3, except for the gradient used: Gradient solvent A/B=75/25 to 0/100 (v/v) in 20.00 min, then constant for an additional 10.00 min at A/B/C=0/100 (v/v).

Method 6: Identical to method 1, except for the gradient used: solvent A/B/C=35/60/5 to 10/85/5 (v/v/v) in 30.00 min, then constant for an additional 10.00 min at A/B/C=10/85/5 (v/v/v).

The following methods are used for preparative HPLC-purifications:

Method A: Column=Luna C-18. Gradient: 0.1% trifluoroacetic acid in $H_2O/CH_3CN$ (9/1, v/v)/$CH_3CN$=100/0 to 0/100 (v/v) in 30-45 min, depending on the ease of separation. Detection: 210 mm. The appropriate fractions were collected and concentrated (partially) in vacuo.

Method B: Column=Luna C-18. Gradient: $H_2O/CH_3CN$ (9/1, v/v)/$CH_3CN$=80/20 to 0/100 (v/v) in 30-45 min, depending on the ease of separation. Detection: 210 nm.

Example 1

Biphenyl-4-carboxylic acid {1-acetyl-4-[4-(2-dimethylammo-ethoxy-phenyl]-2,2,4-trimethyl-1,2,3,4-tetrahydro-quinolin-6-yl}-amide (a). (2,2,4-Trimethyl-1,2-dihydroquinolin-6-yl)-carbamic acid tert-butyl ester A mixture of N-Boc-1,4-phenylenediamine (75 g), $MgSO_4$ (216 g), 4-tert-butylcathechol (1.8 g) and iodine (4.7 g) in anhydrous acetone (600 ml) was heated under reflux for 20 h. The $MgSO_4$ was removed by filtration and the filtrate was concentrated in vacuo. The residue was chromatographed on a short plug of silicagel using heptane/ethyl acetate=8/2 (v/v) as the eluent to give the product as a brown oil.

Yield: 41 g.

(b). (1-Acetyl-2,2,4-trimethyl-1,2-dihydroquinolin-6-yl)-carbamic acid tert-butyl ester A solution of the compound described in example 1a (41 g) in pyridine (200 ml) and $CH_2Cl_2$ (200 ml) was cooled to 0° C. Acetyl chloride (21 ml) in $CH_2Cl_2$ (50 ml) was added dropwise. After complete addition the mixture was stirred for 3 h at room temperature. Ethyl acetate (2 1) and $H_2O$ (2 1) were added and the organic layer was separated, dried and concentrated in vacuo. The title compound was obtained by crystallization from ethyl acetate.

Yield: 23 g.

(c). 1-Acetyl-6-amino-2,2,4-trimethyl-1,2-dihydroquinoline

The compound described in example 1b (15 g) was stirred in a mixture of $CH_2Cl_2$ and TFA (9/1 (v/v), 300 ml) for 2 h. The reaction mixture was cooled down to 0° C., and the pH adjusted to pH 7 using a 2 M aqueous NaOH solution. The organic layer was separated, washed with brine, dried and concentrated in vacuo to give the crude product that was used without further purification in the next step.

Yield 10.4 g (d). Biphenyl-4-carboxylic acid (1-acetyl-2,2,4-trimethyl-1,2-dihydroquinolin-6-yl)-amide To a solution of the compound described in example 1c (10 g) and DIPEA (40 ml) in $CH_2Cl_2$ (100 ml), was added 4-biphenylcarbonyl chloride (9.8 g) and the resulting mixture was stirred for 18 h at room temperature. Water was added, the organic layer was separated, dried and concentrated in vacuo. The product was crystallized from ethyl acetate.

Yield 15 g (e) Biphenyl-4-carboxylic acid [1-acetyl-4-(4-methoxyphenyl)-2,2,4-trimethyl-1,2,3,4-tetrahydroquinolin-6-yl]-amide While stirring, aluminum trichloride (9.7 g) was added to a mixture of the compound described in example 1d (10.0 g) and anhydrous anisole (50 ml) and the resulting mixture was stirred at 35° C. for 18 h. After this time, water was added at 0° C. and the resulting mixture was extracted with ethyl acetate. The organic layer was separated, dried and partially concentrated in vacuo and the mixture was stored at 0° C. for 18 h. The formed precipitate was collected by filtration and dried in vacuo to give the title compound.

Yield: 7.9 g.

(f). Biphenyl-4-carboxylic acid [1-acetyl-4-(4-hydroxyphenyl)-2,2,4-trimethyl-1,2,3,4-tetrahydro-quinolin-6-yl]-amide To a solution of the compound described in example 1e (7.9 g) in $CH_2Cl_2$ (200 ml) at 0° C. was added a solution of boron tribromide (5 ml) in $CH_2Cl_2$ (50 ml) and the mixture was kept for 4 h at 0° C. Water (ca 500 ml) was carefully added and the resulting mixture was vigorously stirred. The organic layer was separated, dried and concentrated in vacuo. Crystallization from ethyl acetate afforded the title compound.

Yield: 6.1 g.

(g) Biphenyl-4-carboxylic acid {1-acetyl-4-[4-(2-dimethylamino-ethoxy)-phenyl]-2,2,4-trimethyl-1,2,3,4-tetrahydro-quinolin-6-yl}-amide General procedure A: To a solution of the compound described in example 1f (70 mg) in DMF (2 ml) were added $Cs_2CO_3$ (200 mg) and 2-dimethylamino-ethylchloride hydrochloride (17 mg). The resulting mixture was stirred overnight, after which water and ethyl acetate were added. The organic layer was separated, dried and concentrated in vacuo. The product was purified by preparative HPLC (method A) and lyophilized from a mixture of $CH_3CN$ and water containing TFA to give the corresponding TFA salt.

Yield: 18 mg (TFA salt); MS-ESI: $[M+H]^+=576.6$; HPLC: $R_t=14.96$ min (method 3).

Example 2

Biphenyl-4-carboxylic acid {1-acetyl-4-[4-(2-dimethylamino-propoxy)-phenyl]-2,2,4-trimethyl-1,2,3,4-tetrahydro-quinolin-6-yl}-amide According to general procedure A, the compound described in example 1f (70 mg) was alkylated with 3-dimethylamino-propylchloride hydrochloride (19 mg) and $Cs_2CO_3$ (200 mg) in DMF (2 ml). The product was purified by preparative HPLC (method A) and lyophilized from a mixture of $CH_3CN$ and water containing TFA to give the corresponding TFA salt.

Yield: 58 mg (TFA salt); MS-ESI: $[M+H]^+=590.4$; HPLC: $R_t=15.36$ min (method 3).

Example 3

Biphenyl-4-carboxylic acid {1-acetyl-2,2,4-trimethyl-4-[4-(3-morpholin-4-yl-propoxy)-phenyl]-1,2,3,4-tetrahydro-quinolin-6-yl}-amide According to general procedure A, the compound described in example 1f (70 mg) was alkylated with 3-morpholinopropylchloride (26 mg) and $Cs_2CO_3$ (200 mg) in DMP (2 ml). The product was purified by preparative HPLC (method A) and lyophilized from a mixture of $CH_3CN$ and water containing TFA to give the corresponding TFA salt.

Yield: 56 mg (TFA salt); MS-ESI: $[M+H]^+=631.6$; HPLC: $R_t=15.40$ min (method 3).

Example 4

Biphenyl-4-carboxylic acid {1-acetyl-2,2,4-trimethyl-4-[4-(pyridin-2-ylmethoxy)-phenyl]-1,2,3,4-tetrahydro-quinolin-6-yl}-amide According to general procedure A, the compound described in example 1f (100 mg) was alkylated with 2-picolyl chloride hydrochloride (33 mg) and $CS_2CO_3$ (325 mg) in DMF (5 ml). The product was purified by preparative HPLC (method A) and lyophilized from a mixture of $CH_3CN$ and water containing TFA to give the corresponding TFA salt.

Yield: 60 mg (TFA salt); MS-ESI: $[M+H]^+=596.4$; HPLC: $R_t=19.75$ min (method 2).

Example 5

Biphenyl-4-carboxylic acid {1-acetyl-2,2,4-trimethyl-4-[4-(1-methyl-piperidin-3-ylmethoxy)phenyl]-1,2,3,4-tetrahydro-quinolin-6-yl}-amide According to general procedure A, the compound described in example 1f (100 mg) was alkylated with 3-chloromethyl-1-methylpiperidine hydrochloride (33 mg) and $Cs_2CO_3$ (325 mg) in DMF (5 ml). The product was purified by preparative HPLC (method A) and lyophilized from a mixture of $CH_3CN$ and water containing TFA to give the corresponding TFA salt.

Yield: 60 mg (TFA salt); MS-ESI: $[M+H]^+=615.4$; HPLC: $R_t=16.70$ min (method 2).

Example 6

Biphenyl-4-carboxylic acid {1-acetyl-4-[4-(2-diethylamino-ethoxy)-phenyl]-2,2,4-trimethyl-1,2,3,4-tetrahydro-quinolin-6-yl}-amide According to general procedure A, the compound described in example 1f (100 mg) was alkylated with 2-diethylamino-ethyl chloride hydrochloride (35 mg) and $Cs_2CO_3$ (325 mg) in DMF (5 ml). The product was purified by preparative HPLC (method A) and lyophilized from a mixture of $CH_3CN$ and water containing TEA to give the corresponding TFA salt.

Yield, 67 mg (TFA salt); MS-ESI: $[M+H]^+=604.4$; HPLC: $R_t=16.38$ min (method 2).

Example 7

Biphenyl-4-carboxylic acid {1-acetyl-2,2,4-trimethyl-4-[4-(pyridin-4-ylmethoxy)-phenyl]-1,2,3,4-tetrahydro-quinolin-6-yl}-amide According to general procedure A, the compound described in example 1f (100 mg) was alkylated with 4 picolylchloride hydrochloride (33 mg) and $Cs_2CO_3$ (325 mg) in DMF (5 ml). The product was purified by preparative HPLC (method A) and lyophilized from a mixture of $CH_3CN$ and water containing TFA to give the corresponding TFA salt.

Yield: 61 mg (TFA salt); MS-ESI: $[M+H]^+=596.4$; HPLC: $R_t=16.64$ min (method 2).

Example 8

Morpholine-1-carboxylic acid [3-(4-{1-acetyl-6-[biphenyl-4-carbonyl)-amino]-2,2,4-trimethyl-1,2,3,4-tetrahydro-quinolin-4-yl}-phenoxy)-propyl]-amide According to general procedure A, the compound described in example 1f (100 mg) was alkylated with morpholine-4-carboxylic acid (3-chloropropyl)amide (53 mg) and $Cs_2CO_3$ (325 mg) in DMF (5 ml). The product was purified by preparative HPLC (method A) and lyophilized from a mixture of $CH_3CN$ and water.

Yield: 95 mg, MS-ESI: $[M+H]^+=675.6$; HPLC: $R_t=18.24$ min (method 3).

Example 9

Biphenyl-4-carboxylic acid {1-acetyl-4-[4-(2-azepan-1-yl-ethoxy)-phenyl]-2,2,4-trimethyl-1,2,3,4-tetrahydro-quinolin-6-yl}-amide According to general procedure A, the compound described in example 1f (100 mg) was alkylated with 2-(hexamethyleneimino)ethyl chloride hydrochloride (42 mg) and $Cs_2CO_3$ (325 mg) in DMF (5 ml). The product was purified by preparative HPLC (method A) and lyophilized from a mixture of $CH_3CN$ and water containing TFA to give the corresponding TFA salt.

Yield: 60 mg (TFA salt); MS-ESI: $[M+H]^+=630.6$; HPLC: $R_t=17.25$ min (method 2).

Example 10

Biphenyl-4-carboxylic acid {1-acetyl-2,2,4-trimethyl-4-[4-(pyridin-3-ylmethoxy)-phenyl]-1,2,3,4-tetrahydro-quinolin-6-yl}-amide According to general procedure A, the compound described in example 1f (1.0 g) was alkylated with 3-picoloyl-chloride hydrochloride (488 mg) and $Cs_2CO_3$ (3.2 mg) in DMF (10 ml). The product was purified by preparative HPLC (method A) and lyophilized from a mixture of $CH_3CN$ and water containing TFA to give the corresponding TFA salt.

Yield: 884 mg (CFA salt); MS-ESI: $[M+H]^+=596A$; HPLC: $R_t=16.55$ min (method 3).

Example 11

Biphenyl-4-carboxylic acid [1-acetyl-4-(4-carbamoylmethoxy-phenyl-2,2,4-trimethyl-1,2,3,4-tetrahydro-quinolin-6-yl]-amide According to general procedure A, the compound described in example 1f (100 mg) was alkylated with 2-chloroacetamide (24 mg) and $Cs_2CO_3$ (325 mg) in DMF (5 ml). The product was purified by preparative HPLC (method A) and lyophilized from a mixture of $CH_3CN$ and water containing TEA to give the corresponding TFA salt Yield: 40 mg; MS-ESI: $[M+H]^+=562.6$; HPLC: $R_t=21.63$ min (method 2).

Example 12

Biphenyl-4-carboxylic acid [1-acetyl-4-(4-allylcarbamoylmethoxy-phenyl-2,2,4-trimethyl-1,2,3,4-tetrahydro-quinolin-6-yl]-amide (a). (4-{1-Acetyl-6-[(biphenyl-4-carbonyl)amino]-2,2,4-trimethyl-1,2,3,4-tetrahydro-quinolin-4-yl}phenoxy)acetic acid tert-butyl ester A mixture of the compound described in example 1f (2.58 g), tert-butyl bromoacetate (826 μl), $K_2CO_3$ (2.8 g) and acetone (100 ml) was stirred for 18 h at 50° C. The solids were removed by filtration and the filtrate was concentrated in vacuo to give the product that was used without further purification in the next step.

Yield: 3.2 g (b). (4-{1-Acetyl-6-[(biphenyl-4-carbonyl)amino]-2,2,4-trimethyl-1,2,3,4-tetrahydro-quinolin-4-yl}phenoxy)acetic acid The compound described in example 12a (3.2 g) was stirred in a mixture of $CH_2Cl_2$ and TFA (9/1 (v/v), 100 ml) for 3 h. Toluene (100 ml) was added and the mixture was concentrated in vacuo to give the crude product, that was used without further purification.

Yield: 3.3 g (c). Biphenyl-4-carboxylic acid [1-acetyl-4-(4-allylcarbamoylmethoxy-phenyl)-2,2,4-trimethyl-1,2,3,4-tetrahydro-quinolin-6-yl]-amide General procedure B: To a solution of the compound described in example 12b (82 mg), allylamine (37 mg) and DIPEA (226 μl) in $CH_2Cl_2$ (5 ml) was added TBTU (84 mg) at room temperature. If the reaction did not reach completion after 18 h, more TBTU and DIPEA were added. After completion of the reaction water was added, the organic layer was separated, washed with brine, dried and concentrated in vacuo. The title compound was purified by preparative HPLC (method A).

Yield: 48 mg, MS-ESI: $[M+H]^+=602.4$; HPLC: $R_t=18.19$ min (method 4).

Example 13

Biphenyl-4-carboxylic acid {1-acetyl-4-[4-(isopropylcarbamoyl-methoxy)-phenyl]-2,2,4-trimethyl-1,2,3,4-tetrahydro-quinolin-6-yl}-amide According to general procedure B, the compound described in example 12b (82 mg) was treated with isopropylamine (38 mg), DIPEA (226 μl) and TBTU (84 mg) in $CH_2Cl_2$ (5 ml). The title compound was purified by preparative HPLC (method A).

Yield: 45 mg; MS-ESI: $[M+H]^+=604.6$; HPLC: $R_t=18.63$ min (method 4).

Example 14

Biphenyl-4-carboxylic acid [1-acetyl-4-(4-diethylcarbamoylmethoxy-phenyl)-2,2,4-trimethyl-1,2,3,4-tetrahydro-quinolin-6-yl]-amide According to general procedure B, the compound described in example 12b (82 mg) was treated with diethylamine hydrochloride (47 mg), DIPEA (226 μl) and TBTU (84 mg) in CH$_2$Cl$_2$ (5 ml). The title compound was purified by preparative HPLC (method A).

Yield: 51 mg, MS-ESI: [M+H]$^+$=618.4; HPLC: R$_t$=19.09 min (method 4).

Example 15

Biphenyl-4-carboxylic acid [1-acetyl-2,2,4-trimethyl-4-(4-{[(pyridin-4-ylmethyl)-carbamoyl]-methoxy}-phenyl)-1,2,3,4-tetrahydro-quinolin-6-yl]-amide According to general procedure B, the compound described in example 12b (82 mg) was treated with 4-picolylamine (70 mg), DIPEA (226 μl) and TBTU (84 mg) in CH$_2$Cl$_2$ (5 ml). The title compound was purified by preparative HPLC (method A) and lyophilized from a mix of CH$_3$CN and water containing TFA to give the corresponding TFA salt.

Yield: 52 mg (TFA salt); MS-ESI: [M+H]$^+$=653.6; HPLC: R$_t$=11.31 min (method 4).

Example 16

Biphenyl-4-carboxylic acid [1-acetyl-4-(4-{[(furan-2-ylmethyl)-carbamoyl]-methoxy}-phenyl 2,2,4-trimethyl-1,2,3,4-tetrahydro-quinolin-6-yl]-amide According to general procedure B, the compound described in example 12b (82 mg) was treated with 2-furfurylamine (63 mg), DIPEA (226 μl) and TBTU (84 mg) in CH$_2$Cl$_2$ (5 ml). The title compound was purified by preparative HPLC (method A).

Yield: 50 mg; MS-ESI: [M+H]$^+$=642.6; HPLC: R$_t$=21.31 min (method 3).

Example 17

Biphenyl-4-carboxylic acid (1-acetyl-4-{4-[(2-methoxy-ethylcarbamoyl)-methoxy]-phenyl}-2,2,4-trimethyl-1,2,3,4-tetrahydro-quinolin-6-yl)-amide According to general procedure B, the compound described in example 12b (82 mg) was treated with 2-methoxyethylamine (49 mg), DIPEA (226 μl) and TBTU (84 mg) in CH$_2$Cl$_2$ (5 ml). The title compound was purified by preparative HPLC (method A).

Yield: 34 mg; MS-ESI: [+H]$^+$=620.4; HPLC: R$_t$=19.70 min (method 3).

Example 18

Biphenyl-4-carboxylic acid {1-acetyl-4-[4-(benzylcarbamoyl-methoxy)-phenyl]-2,2,4-trimethyl-1,2,3,4-tetrahydro-quinolin-6-yl}-amide According to general procedure B, the compound described in example 12b (82 mg) was treated with benzylamine (49 mg), DIPEA (226 μl) and TBTU (84 mg) in CH$_2$Cl$_2$ (5 ml). The title compound was purified by preparative HPLC (method A).

Yield: 53 mg, MS-ESI: [M+H]$^+$=652.6; HPLC: R$_t$=22.26 min (method 3).

Example 19

Biphenyl-4-carboxylic acid (1-acetyl-{4-[(2-dimethylamino-ethylcarbamoyl)-methoxy]-phenyl}-2,2,4-trimethyl-1,2,3,4-tetrahydro-quinolin-6-yl)-amide According to general procedure B, the compound described in example 12b (82 mg) was treated with N,N-dimethylethylenediamine (49 mg), DIPEA (226 μl) and TBTU (84 mg) in CH$_2$Cl$_2$ (5 ml). The title compound was purified by preparative HPLC (method A). Lyophilization from a mixture of aqueous HCl and 1,4-dioxane afforded the title compound as a HCl-salt Yield: 11 mg (HCl-salt); MS-ESI: [M+H]$^+$=633.4; HPLC: R$_t$=13.74 min (method 3).

Example 20

Biphenyl-4-carboxylic acid [1-acetyl-2,2,4-trimethyl-4-(4-methylcarbamoylmethoxy-phenyl)-1,2,3,4-tetrahydro-quinolin-6-yl]-amide According to general procedure B, the compound described in example 12b (82 mg) was treated with methylamine hydrochloride (20 mg), DIPEA (226 μl) and TBTU (84 mg) in CH$_2$Cl$_2$ (5 ml). The title compound was purified by preparative HPLC (method A).

Yield: 35 mg, MS-ESI: [M+H]$^+$=576.4; HPLC: R$_t$=19.25 min (method 3).

Example 21

Biphenyl-4-carboxylic acid {1-acetyl-2,2,4-trimethyl-4-[4-(2-morpholin-4-yl-2-oxo-ethoxy)-phenyl]-1,2,3,4-tetrahydro-quinolin-6-yl}-amide According to general procedure B, the compound described in example 12b (110 mg) was treated with morpholine (74 mg), DIPEA (296 μl) and TBTU (109 mg) in CH$_2$Cl$_2$ (5 ml). The title compound was purified by preparative HPLC (method A).

Yield: 85 mg; MS-ESI: [M+H]$^+$=632.4; HPLC: R$_t$=12.48 min (method 3).

Example 22

N-{1-Acetyl-2,2,4-trimethyl-4-[4-(3-morpholin-4-yl-propoxy)-phenyl]-1,2,3,4-tetrahydro-quinolin-6-yl}-5-bromo-2-methylamino-benzamide (a). (1-Acetyl-2,2,4-trimethyl-1,2-dihydro-quinolin-6-yl)-carbamic acid 9-fluoren-ylmethyl ester To a solution of the compound described in example 1c (17 g) and DIPEA (40 ml) in CH$_2$Cl$_2$ (100 ml), was added FmocCl (25 g) and the resulting mixture was stirred for 18 h at room temperature. Ethyl acetate (ca 200 ml) and water (150 ml) were added, the organic layer was separated, dried and concentrated in vacuo. The title compound was purified by chromatography on silicagel using CH$_2$Cl$_2$ as the eluent.

Yield: 16.6 g (b) [1-Acetyl-4-(4-methoxyphenyl)-2,2,4-trimethyl-1,2,3,4-tetrahydroquinolin-6-yl]-carbamic acid 9-fluorenylmethyl ester While stirring, aluminum trichloride (24.2 g) was added to a mixture of the compound described in example 22a (16.5 g) and anhydrous anisole (150 ml) and the resulting mixture was stirred at 35° C. for 18 h. After this time, water was added at 0° C. and the resulting mixture was extracted with ethyl acetate. The organic layer was separated, dried and partially concentrated in vacuo and the mixture was stored at 0° C. for 18 h. The formed precipitate was collected by filtration and dried in vacuo to give the title compound.
Yield: 10.1 g.

(c) [1-Acetyl-4-(4-hydroxyphenyl)-2,2,4-trimethyl-1,2,3,4-tetrahydroquinolin-6-yl]-carbamic acid 9-fluorenylmethyl ester To a mixture of the compound described in example 22b (10.1 g) in anhydrous $CH_2Cl_2$ (500 ml) was added dropwise boron tribromide (5.05 ml) and the resulting mixture was stirred for 2.5 h at room temperature. The reaction was quenched with ice water at 0° C. and $CH_2Cl_2$ was added. The organic layer was separated, dried and stored at 4° C. for 20 h. The formed solids were collected by filtration and dried in vacuo to give the crude product that was used without further purification.
Yield: 12.5 g.

(d). 1-Acetyl-6-amino-2,2,4-trimethyl-4-[4-(3-morpholin 1-propoxy)-phenyl]-1,2,3,4-tetrahydroquinoline A mixture of the compound described in example 22c (1.0 g), $Cs_2CO_3$ (1.8 g), 4-(3-chloropropyl)morpholine (330 mg) and DMF (5 ml) was stirred at 60° C. for 18 h. Water was added and the mixture was extracted with $CH_2Cl_2$. The organic layer was dried and concentrated in vacuo. The title compound was purified by chromatography on silicagel using $CH_2Cl_2$/2% concentrated ammonia in MEOH=1/0=>9/1 (v/v) as the eluent.
Yield 527 mg (e). N-{1-Acetyl-2,2,4-trimethyl-4-[4-(3-morpholin-4-yl-propoxy)-phenyl]-1,2,3,4-tetrahydro-quinolin-6-yl}-5-bromo-2-methylamino-benzamide General procedure C: To a solution of the compound described in example 22d (132 mg), 5-bromo-2-methylamino benzoic acid (101 mg) and DIPEA (255 µl) in $CH_2Cl_2$ (3 ml) was added HATU (166 mg) at room temperature. The reaction mixture was stirred for 18 h at room temperature. Ethyl acetate (15 ml) and 2 M aqueous NaOH (15 ml) were added. The organic layer was separated and washed with 2 M aqueous NaOH (10 ml) and water (15 ml), dried and concentrated in vacuo. The title compound was purified by preparative HPLC (method A).
Yield: 69.8 mg; MS-BSI: $[M+H]^+$=663.4; HPLC: $R_t$=14.65 min (method 3).

Example 23

N-{1-Acetol-2,2,4-trimethyl-4-[4-(3-morpholin-4-yl-propoxy)-phenyl]-1,2,3,4-tetrahydro-quinolin-6-yl}-3,5-dichloro-2,6-dimethoxy-benzamide According to general procedure C, the compound described in example 22d (132 mg) was acylated with 3,5-dichloro-2,6-dimethoxybenzoic acid (110 mg), DIPEA (255 µl) and HATU (166 mg) in $CH_2Cl_2$ (3 ml). The title compound was purified by preparative HPLC (method A).
Yield: 68.3 mg; MS-ESI: $[M+H]^+$=684.3; HPLC: $R_t$=13.45 min (method 3).

Example 24

Biphenyl-4-carboxylic acid [1-acetyl-4-(4-{2[-(furan-2-ylmethyl)-amino]-ethoxy}-phenyl)-2,2,4-trimethyl-1,2,3,4-tetrahydro-quinolin-6-yl]-amide (a). (4-{1-Acetyl-6-[(biphenyl-4-carbonyl)amino]-2,2,4-trimethyl-1,2,3,4-tetrahydro-quinolin-4-yl}-phenoxy)acetic acid ethyl ester A mixture of the compound described in example 1f (1 g), ethyl bromoacetate (220 µl), $K_2CO_3$ (850 mg) and acetone (25 ml) was stirred for 6 h at 50° C. The solids were removed by filtration and the filtrate was concentrated in vacuo to give the product that was used without farther purification in the next step.
Yield: 1.2 g (b). Biphenyl-4-carboxylic acid {1-acetyl-4-[4-(2-hydroxyethoxy phenyl]-2,2,4-trimethyl-1,2,3,4-tetrahydroquinolin-6-yl}-amide To a solution of the compound described in example 24a (1.2 g) in THF (10 ml) at 0° C. was carefully added $LiALH_4$ (78 mg), and the resulting mixture was stirred for 3 h at room temperature. Ethyl acetate (50 ml) was added dropwise, followed by water (50 ml). The aqueous layer was separated and extracted with ethyl acetate (50 ml) and the combined organic fractions were washed with brine. The organic layer was dried and concentrated in vacuo to give the product that was used without further purification in the next step.
Yield: 1 g (c). Methanesulfonic acid 2-(4-{1-acetyl-6-[(biphenyl-4-carbonyl)amino]-2,2,4-trimethyl-1,2,3,4-tetrahydroquinolin-4-yl}phenoxy)ethyl ester To a solution of the compound described in example 24b (1 g) and DIPEA (1.7 ml) in $CH_2Cl_2$ (15 ml), was added dropwise a solution of methanesulfonyl chloride (310 µl) in $CH_2Cl_2$ (5 ml). After 2 h, water was added, the organic layer separated, dried and concentrated in vacuo. The title compound was purified by chromatography on silicagel using heptane/ethyl acetate=9/1=>1/1 (v/v) as the eluent.
Yield: 870 mg (d). Biphenyl-4-carboxylic acid [1-acetyl-4-(4-{2-[(furan-2-ylmethyl)-amino]-ethoxy}-phenyl)-2,2,4-trimethyl-1,2,3,4-tetrahydro-quinolin-6-yl]-amide General procedure D: To a solution of the compound described in example 24c (87 mg) in $CH_3CN$ (5 ml) was added 2-furfurylamine (107 mg) and the resulting mixture was stirred at 70° C. for 18 h. The mixture was concentrated in vacuo and the product was purified by preparative HPLC (method A) and lyophilized from a mixture of $CH_3CN$ and water containing TFA to give the corresponding TFA salt.

Yield: 47 mg (TFA salt); MS-ESI: $[M+H]^+=628.6$; HPLC: $R_t=11.53$ mm (method 4).

Example 25

Biphenyl-4-carboxylic acid (1-acetyl-4{-4-[2-(2-hydroxy-1,1-dimethyl-ethylamino)-ethoxy]-phenyl}-2,2,4-trimethyl-1,2,3,4-tetrahydro-quinolin-6-yl)-amide According to general procedure D, the compound described in example 24c (87 mg) was treated with 2-amino-2-methyl-propan-1-ol (100 mg) in $CH_3CN$ (5 ml). The title compound was purified by preparative HPLC (method A) and lyophilized from a mixture of $CH_3CN$ and water containing TFA to give the corresponding TFA salt Yield: 21 mg (TFA salt); MS-ESI: $[M+H]^+=619.8$; HPLC: $R_t=10.95$ min (method 4).

Example 26

Biphenyl-4-carboxylic acid [1-acetyl-2,2,4-trimethyl-4-(4-{2-[(pyridin-3-ylmethyl)-amino]-ethoxy}-phenyl)-1,2,3,4-tetrahydro-quinolin-6-yl]-amide According to general procedure D, the compound described in example 24c (87 mg) was treated with 3-aminomethylpyridine (119 mg) in $CH_3CN$ (5 ml). The title compound was purified by preparative HPLC (method A) and lyophilized from a mixture of $CH_3CN$ and water containing TFA to give the corresponding TFA salt Yield: 40 mg (TFA salt); MS-ESI: $[M+H]+^=639.4$; HPLC: $R_t4=10.15$ min (method 4).

Example 27

Biphenyl-4-carboxylic acid (1-acetyl-4-{4-[2-(2-hydroxy-ethylamino)ethoxy]-phenyl}-2,2,4-trimethyl-1,2,3,4-tetrahydro-quinolin-6-yl)-amide According to general procedure D, the compound described in example 24c (100 mg) was treated with ethanolamine (100 mg) in $CH_3CN$ (5 ml). The title compound was purified by preparative HPLC (method A) and lyophilized from a mixture of $CH_3CN$ and water containing TFA to give the corresponding TFA salt Yield: 50 mg (TFA salt); MS-ESI: $[+H]^+=592.6$; HPLC: $R_t=10.32$ min (method 1).

Example 28

Biphenyl-4-carboxylic acid (1-acetyl-4-{4-[2-(2-amino-ethylamino)-ethoxy]-phenyl}-2,2,4-trimethyl-1,2,3,4-tetrahydro-quinolin-6-yl)-amide According to general procedure D, the compound described in example 24c (100 mg) was treated with ethylenediamine (110 mg) in $CH_3CN$ (5 ml). The title compound was purified by preparative HPLC (method A) and lyophilized from a mixture of $CH_3CN$ and water containing TFA to give the corresponding TEA salt Yield: 45 mg (TFA salt); MS-ESI: $[M+H]^+=591.4$; HPLC: $R_t=7.04$ min (method 1).

Example 29

Biphenyl-4-carboxylic acid {1-acetyl-2,2,4-trimethyl-4-[4-(2-piperazin-1-yl-ethoxy)-phenyl]-1,2,3,4-tetrahydro-quinolin-6-yl}-amide According to general procedure D, the compound described in example 24c (100 mg) was treated with piperazine (140 mg) in $CH_3CN$ (5 ml). The title compound was purified by preparative HPLC (method A) and lyophilized from a mixture of $CH_3CN$ and water containing TFA to give the corresponding TFA salt Yield: 95 mg (TFA salt); MS-ESI: $[M+H]^+=617.6$; HPLC: $R_t=9.54$ min (method 1).

Example 30

Morpholine-4-carboxylic acid (3-{4-[1-acetyl-6-(3,5-dichloro-2,6-dimethoxy-benzoylamino)-2,2,4-trimethyl-1,2,3,4-tetrahydro-quinolin-4-yl]-phenoxy}-propyl)-amide (a). Morpholine-4-carboxylic acid (3-{4-[1-acetyl-6-amino-2,2,4-trimethyl-1,2,3,4-tetrahydro-quinolin-4-yl]-phenoxy}-propyl)-amide According to the same procedure described in example 22d, the compound described in example 22c (1.0 g), was alkylated (with concomitant removal of the Fmoc protective group) with morpholine-4-carboxylic acid (3-chloropropyl) amide (448 mg) using $Cs_2CO_3$ (1.8 g) in DMF (5 ml). The title compound was purified by chromatography on silicagel using $CH_2Cl_2$/2% concentrated ammonia in MeOH=1/0=>9/1 (v/v) as the eluent Yield: 894 mg.

(b). Morpholine-4-carboxylic acid (3-({[4-acetyl-6-(3,5-dichloro-2.6 dimethoxy-benzylamino-2,2,4-trimethyl-1,2,3,4-tetrahydro-quinolin-4-yl]-phenoxy}-propyl)-amide According to general procedure C, the compound described in example 30a (228 mg) was acylated with 3,5-dichloro-2,6-dimethoxybenzoic acid (230 mg), DIPEA (558 μl) and HATU (609 mg) in $CH_2Cl_2$ (5 ml). The title compound was purified by preparative HPLC (method A).

Yield: 102 mg, MS-ESI: $[M+H]^+=727.4$; HPLC: $R_t=22.37$ min (method 2).

Example 31

N-{1-Acetyl-2,2,4-trimethyl-4-[4-(2-morpholin-4-yl-ethoxy)-phenyl]-1,2,3,4-tetrahydro-quinolin-6-yl}-3,5-dibromo-benzamide (a). 1-Acetyl-6-amino-2,2,4-trimethyl-4-[4-(2-morpholin-4-yl-ethoxy)-phenyl]-1,2,3,4-tetrahydro-quinoline A mixture of the compound described in example 22c (1.0 g), $Cs_2CO_3$ (1.8 g), N-(2-chloroethyl)-morpholine hydrochloride (375 mg), and DMF (5 ml) was stirred at 60° C. for 18 h. The reaction did not reach completion and additional amounts of $Cs_2CO_3$ and N-(2-chloroethyl)-morpholine hydrochloride were added. After the reaction was complete, water was added and the mixture was extracted with $CH_2Cl_2$. The organic layer was dried and concentrated in vacuo. The title compound was purified by chromatography on silicagel using $CH_2Cl_2$/2% concentrated ammonia in MEOH=1/0=>9/1 (v/v) as the eluent Yield: 905 mg.

(b). N-{1-Acetyl-2,2,4-trimethyl-4-[4-(2-morpholin-4-yl-ethoxy)-phenyl]-1,2,3,4-tetrahydro-quinolin-6-yl}-3,5-dibromo-benzamide According to general procedure C, the compound described in example 31a (157 mg) was acylated with 3,5-dibrombenzoic acid (150 mg), DIPEA (313 µl) and HATU (204 mg) in $CH_2Cl_2$ (5 ml). The title compound was purified by preparative HPLC (method A).

Yield: 71 mg (A salt); MS-ESI: $[M+H]^+=700.2$; HPLC: $R_t=16.12$ min (method 2).

Example 32

N-({-Acetyl-2,2,4-trimethyl-4-[4-(2-morpholin-4-yl-ethoxy)-phenyl]-1,2,3,4-tetrahydro-quinolin-6-yl}-2-chloro-benzamide According to general procedure C, the compound described in example 31a (150 mg) was acylated with 2-chlorobenzoic acid (81 mg), DIPEA (299 µl) and HATU (195 mg) in $CH_2Cl_2$ (6 ml). The title compound was purified by preparative HPLC (method A).

Yield: 162 mg (TFA salt); MS-ESI: $[M+H]^+=576.4$; HPLC: $R_t=9.37$ min (method 2).

Example 33

N-{1-Acetyl-2,2,4-trimethyl-4-[4-(2-morpholin-4-yl-ethoxy)-phenyl]-1,2,3,4-tetrahydro-quinolin-6-yl}-3,5-dimethyl-benzamide According to general procedure C, the compound described in example 31a (200 mg) was acylated with 3,5-dimethylbenzoic acid (103 mg), DIPEA (399 µl) and HATU (260 mg) in $CH_2Cl_2$ (7.5 ml). The title compound was purified by preparative HPLC (method A).

Yield: 57.5 mg (TFA salt); MS-ESI: $[M+H]^+=570.4$; HPLC: $R_t=12.62$ min (method 2).

Example 34

N-{1-Acetyl-2,2,4-trimethyl-4-[4-(2-morpholin-4-yl-ethoxy)-phenyl]-1,2,3,4-tetrahydro-quinolin-6-yl}-2,5-dichloro-benzamide According to general procedure C, the compound described in example 31a (200 mg) was acylated with 2,5-dichlorobenzoic acid (131 mg), DIPEA (399 µl) and HATU (260 mg) in $CH_2Cl_2$ (7.5 ml). The title compound was purified by preparative HPLC (method A).

Yield: 130 mg (TFA salt); MS-ESI: $[+H]^+=610.2$; HPLC: $R_t=11.70$ min (method 2).

Example 35

N-{1-Acetyl-2,2,4-trimethyl-4-[4-(2-morpholin-4-yl-ethoxy)-phenyl]-1,2,3,4-tetrahydro-quinolin-6-yl}-5-methyl-2-nitro-benzamide According to general procedure C, the compound described in example 31a (157 mg) was acylated with 5-methyl-2-nitrobenzoic acid (97.3 mg), DIPEA (313 µl) and HATU (204 mg) in $CH_2Cl_2$ (5 ml). The title compound was purified by preparative HPLC (method A).

Yield: 80 mg (TFA salt); MS-ESI: $[M+H]^+=601.4$; HPLC: $R_t=9.95$ min (method 2).

Example 36

N-{1-Acetyl-2,2,4-trimethyl-4-[4-(2-morpholin-4-yl-ethoxy)-phenyl]-1,2,3,4-tetrahydro-quinolin-6-yl}-benzamide According to general procedure C, the compound described in example 31a (157 mg) was acylated with benzoic acid (65.6 mg), DIPEA (313 µl) and HATU (204 mg) in $CH_2Cl_2$ (5 ml). The title compound was purified by preparative HPLC (method A).

Yield: 59 mg (TFA salt); MS-ESI: $[M+H]^+=542.4$; HPLC: $R_t=9.99$ min (method 2).

Example 37

N-{1-Acetal-2,2,4-trimethyl-4-[4-(2-morpholin-4-ethoxy)-phenyl]-1,2,3,4-tetrahydro-quinolin-6-yl}-4-tert-butyl-benzamide According to general procedure C, the compound described in example 31a (161 mg) was acylated with 4-tert-butylbenzoic acid (99 mg), DIPEA (322 µl) and HATU (210 mg) in $CH_2Cl_2$ (5 ml). The title compound was purified by preparative HPLC (method A).

Yield: 80 mg (TFA salt); MS-ESI: $[M+H]^+=598.2$; HPLC: $R_t=15.39$ min (method 2).

Example 38

N-{-Acetyl-2,2,4-trimethyl-4-[4-(2-morpholin-4-yl-ethoxy)-phenyl]-1,2,3,4-tetrahydro-quinolin-6-yl}-2,3-dichloro-benzamide According to general procedure C, the compound described in example 31a (161 mg) was acylated with 2,3-dichlorobenzoic acid (106 mg), DIPEA (322 µl) and HATU (210 mg) in $CH_2Cl_2$ (5 ml). The title compound was purified by preparative HPLC (method A).

Yield: 113 mg (TFA salt); MS-ESI: $[M+H]^+=610.2$; HPLC: $R_t=11.42$ min (method 2).

Example 39

N-{1-Acetyl-2,2,4-trimethyl-4-[4-(2-morpholin-4-yl-ethoxy)-phenyl]-1,2,3,4-tetrahydro-quinolin-6-yl}-4-bromo-benzamide According to general procedure C, the compound described in example 31a (260 mg) was acylated with 4-bromobenzoic acid (179 mg), DIPEA (517 µl) and HATU (338 mg) in $CH_2Cl_2$ (5 ml). The title compound was purified by preparative HPLC (method A).

Example 40

N-{1-Acetyl-2,2,4-trimethyl-4-[4-(2-morpholin-4-yl-ethoxy)-phenyl]-1,2,3,4-tetrahydro-quinolin-6-yl}-methoxy-3-methyl-benzamide According to general procedure C, the compound described in example 31a (260 mg) was acylated with 4-methoxy-3-methylbenzoic acid (148 mg), DIPEA (517 µl) and HATU (338 mg) in $CH_2Cl_2$ (5 ml). The title compound was purified by preparative HPLC (method A).

Yield: 158 mg (TFA salt); MS-ESI: $[M+H]^+=586.2$; HPLC: $R_t=11.49$ min (method 2).

Example 41

N-{1-Acetyl-2,2,4-trimethyl-4-[4-(2-morpholin-4-yl-ethoxy)-phenyl]-1,2,3,4-tetrahydro-quinolin-6-yl}-4-dimethylamino-benzamide According to general procedure C, the compound described in example 31a (260 mg) was acylated with 4-dimethylaminobenzoic acid (147 mg), DIPEA (517 pd) and HATU (338 mg) in $CH_2Cl_2$ (5 ml). The title compound was purified by preparative HPLC (method A).

Yield: 95 mg (TFA salt); MS-ESI: $[M+H]^+=585.2$; HPLC: $R_t=9.53$ min (method 2).

Example 42

N-{1-Acetyl-2,2,4-trimethyl-4-[4-(2-morpholin-4-yl-ethoxy)-phenyl]-1,2,3,4-tetrahydro-quinolin-6-yl}-3-trifluoromethyl-benzamide To a solution of the compound described in example 31a (260 mg) and pyridine (500 µl) in toluene (4.5 ml) was added 3-(trifluoromethyl)benzoyl chloride (185 mg). Ethyl acetate (15 ml) and water (15 ml) were added. The organic layer was separated and washed with water (15 ml), dried and concentrated in vacuo. The title compound was purified by preparative HPLC (method A).

Yield: 200 mg (TFA salt); MS-ESI: $[M+H]^+=610.2$; HPLC: $R_t=13.23$ min (method 2).

Example 43

N-{1-Acetyl-2,2,4-trimethyl-4-[4-(2-morpholin-4-yl-ethoxy)-phenyl]-1,2,3,4-tetrahydro-quinolin-6-yl}-3-nitro-benzamide To a solution of the compound described in example 31a (260 mg) and pyridine (500 µl) in toluene (4.5 ml) was added 3-nitrobenzoyl chloride (165 mg). Ethyl acetate (15 ml) and water (15 ml) were added. The organic layer was separated and washed with water (15 ml), dried and concentrated in vacuo. The title compound was purified by preparative HPLC (method A).

Yield: 167 mg (TFA salt); MS-ESI: $[M+H]^+=587.4$; HPLC: $R_t=10.28$ min (method 2).

Example 44

CHO-FSH In Vitro Bioactivity

FSH activity of compounds were tested in Chinese Hamster Ovary (CHO) cells stably transfected with the human FSH receptor and cotransfected with a cAMP responsive element (CRE)/promotor directing the expression of a firefly luciferase reporter gene. Binding of ligand to the Gs-coupled FSH receptor will result in an increase of cAMP, which in turn will induce an increased transactivation of the luciferase reporter construct. To test antagonistic properties recombinant FSH in a concentration that induces approximately 80% of the maximal stimulation of cAMP accumulation in the absence of test compound was added (rec-hFSH; 10 mU/ml). The luciferase signal was quantified using a luminescence counter. For test compounds, $EC_{50}$ values (concentration of test compound causing half-maximal (50%) stimulation or reduction) were calculated. For that purpose the software program GraphPad PRISM, version 3.0 (GraphPad software Inc., San Diego) was used.

Compounds of all examples exhibited an $EC_{50}$ ($IC_{50}$) value of less than $10^{-5}$ M in either an agonistic or an antagonistic assay set-up or both. The compounds of examples 3, 4, 7, 10-13, 16, 36, 37, 39, 41 and 42 showed an $EC_{50}$ ($IC_{50}$) of less than $10^{-7}$ M in at least one of the assays.

The invention claimed is:

1. A tetrahydroquinoline derivative according to Formula 1,

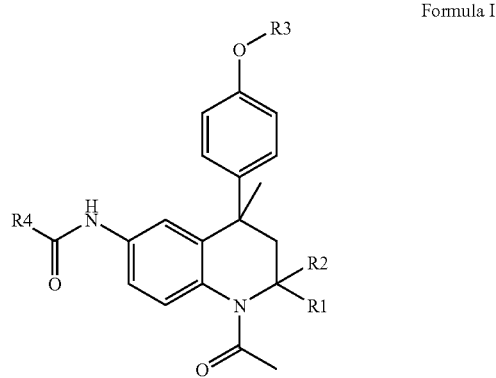

Formula I or a pharmaceutically acceptable salt thereof, wherein
$R^1$ and $R^2$ are H or $R^1$ and $R^2$ are Me;
$R^3$ is (2-6C)heterocycloalkyl(1-4C)alkyl, (2-5C)heteroaryl(1-4C)alkyl, (6C)aryl(1-4C) alkyl, (1-4C)(di)alkylaminocarbonylamino(2-4C)alkyl, (2-6C)heterocycloalkylcarbonylamino(2-4C)alkyl, $R^5$-(2-4C)alkyl or $R^5$-carbonyl(1-4C)alkyl;
$R^4$ is (2-5C)heteroaryl, (6C)aryl, (3-8C)cycloalkyl, (2-6C)heterocycloalkyl or (1-6C)alkyl; and
$R^5$ is (di)(1-4C)alkylamino, (1-4C)alkoxy, amino, hydroxy, (6C)arylamino, (di)(3-4C)alkenylamino, (2-5C)heteroaryl(1-4C)alkylamino, (6C)aryl(1-4C)alkylamino, (di)[(1-4C)alkoxy(2-4C)alkyl]amino, (di)[(1-4C)alkylamino(2-4C)alkyl]amino, (di)[amino(2-4C)alkyl]amino or (di)[hydroxy(2-4C)alkyl]amino.

2. The derivative according to claim 1 wherein $R^3$ is (2-6C)heterocycloalkyl(1-4C)alkyl, (2-5C)heteroaryl(1-4C)alkyl, (2-6C)heterocycloalkylcarbonylamino(2-4C)alkyl, $R^5$-(2-4C)alkyl or $R^5$-carbonyl(1-4C)alkyl.

3. The derivative according to claim 2 wherein $R^5$ is (di)(1-4C)alkylamino, amino, (di)(3-4C)alkenylamino, (2-5C)heteroaryl(1-4C)alkylamino or (6C)aryl(1-4C)alkylamino.

4. The derivative according to claim 3 wherein $R^5$ is (di)(1-4C)alkylamino or amino.

5. The derivative according to claim 4 wherein $R^5$ is (di)(1-4C)alkylamino.

6. The derivative according to claim 1 wherein $R^4$ is (6C) aryl.

7. The derivative according to claim 6 wherein $R^3$ is (2-6C)heterocycloalkyl(1-4C)alkyl, (2-5C)heteroaryl(1-4C)alkyl or $R^5$-(2-4C)alkyl.

8. A pharmaceutical composition comprising the tetrahydroquinoline derivative of claim 1 and at least one pharmaceutically suitable auxiliary.

9. A method of fertility regulation comprising administering an FSH receptor activity modulating amount of the pharmaceutical composition of claim 8 to a patient in need thereof, wherein the fertility regulation is contraception in a female.

* * * * *